United States Patent
Mane et al.

(10) Patent No.: US 11,846,021 B2
(45) Date of Patent: Dec. 19, 2023

(54) ANTIMICROBIAL COATINGS

(71) Applicant: UCHICAGO ARGONNE, LLC, Chicago, IL (US)

(72) Inventors: Anil U. Mane, Naperville, IL (US); Jeffrey W. Elam, Elmhurst, IL (US); Seth B. Darling, Chicago, IL (US); Nestor J. Zaluzec, Bolingbrook, IL (US); Alex B. Martinson, Naperville, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

(21) Appl. No.: 17/039,969

(22) Filed: Sep. 30, 2020

(65) Prior Publication Data

US 2022/0098730 A1    Mar. 31, 2022

(51) Int. Cl.
| | | |
|---|---|---|
| *C23C 16/02* | (2006.01) | |
| *C23C 16/40* | (2006.01) | |
| *C23C 16/455* | (2006.01) | |
| *A01N 25/10* | (2006.01) | |
| *A61L 2/18* | (2006.01) | |
| *A01N 59/16* | (2006.01) | |
| *A61L 101/30* | (2006.01) | |
| *A61L 101/24* | (2006.01) | |
| *A61L 101/06* | (2006.01) | |
| *A61L 101/02* | (2006.01) | |

(52) U.S. Cl.
CPC ........ *C23C 16/45527* (2013.01); *A01N 25/10* (2013.01); *A01N 59/16* (2013.01); *A61L 2/18* (2013.01); *C23C 16/0272* (2013.01); *C23C 16/40* (2013.01); *C23C 16/45555* (2013.01); *A61L 2101/02* (2020.08); *A61L 2101/06* (2020.08); *A61L 2101/24* (2020.08); *A61L 2101/30* (2020.08); *A61L 2202/26* (2013.01)

(58) Field of Classification Search
CPC .......... C23C 16/45527; C23C 16/0272; C23C 16/40; C23C 16/45555
See application file for complete search history.

(56) References Cited

U.S. PATENT DOCUMENTS

| | | | |
|---|---|---|---|
| 2007/0065578 A1* | 3/2007 | McDougall | ......... C23C 16/4408 427/248.1 |
| 2013/0022658 A1 | 1/2013 | Lee | |
| 2017/0166456 A1* | 6/2017 | Darling | ................ B01J 20/3291 |
| 2018/0171475 A1* | 6/2018 | Maes | .................. C23C 16/4485 |

FOREIGN PATENT DOCUMENTS

WO    WO-2015/107476 A1    7/2015

OTHER PUBLICATIONS

Castro-Mayorga, et al., "Antiviral properties of silver nanoparticles against norovirus surrogates and their efficacy in coated polyhydroxyalkanoates systems," LWT—Food Science and Technology 79, pp. 503-510 (2017).

(Continued)

*Primary Examiner* — Elizabeth A Burkhart
(74) *Attorney, Agent, or Firm* — Foley & Lardner LLP

(57) ABSTRACT

The sequential infiltration synthesis (SIS) and Atomic Layer Deposition (ALD) of metal and/or metal oxides on personal medical equipment (PPE). The deposited metal and/or metal oxides imbues antimicrobial properties to the PPE.

16 Claims, 22 Drawing Sheets

(56) References Cited

OTHER PUBLICATIONS

Copper Touch Surfaces, "TouchSurfaces Clinical Trials: Bacteria," retrieved from https://coppertouchsurface.org/antimicrobial/bacteria/homepage.html, 3 pages (2020).

Ghaffari, et al., "Inhibition of H1N1 influenza virus infection by zinc oxide nanoparticles: another emerging application of nanomedicine," Journal of Biomedical Science 26, 70, 10 pages (2019).

Kusiak-Nejman, et al., "*E. coli* Inactivation by High-Power Impulse Magnetron Sputtered (HIPIMS) Cu Surfaces," The Journal of Physical Chemistry C 115(43), pp. 21113-21119 (2011).

Lara, et al., "Mode of antiviral action of silver nanoparticles against HIV-1," Journal of Nanobiotehnology 8, 1, 10 pages (2010).

Masango, et al., "Nucleation and Growth of Silver Nanoparticles by AB and ABC-Type Atomic Layer Deposition," The Journal of Physical Chemistry C 118(31), pp. 17655-17661 (2014).

Mizutani, et al., "Anti-Bacterial and Photocatalytic Activities of (Mo0.5, W0.5)O3 with Cu(Mo0.5, W0.5)O4 Prepared by Impregnation Method and Mechanochemical Processing," Journal of the Japan Society of Colour Material 91(3), pp. 89-93 (2018).

Monmoaturapoj, et al., "Antiviral activity of multifunctional composite based on TiO2-modified hydroxyapatite," Materials Science and Engineering: C 92, pp. 96-102 (2018).

Morris, "Self-sanitizing face mask project receives NSF Rapid grant," Northwestern Now, retrieved from https://news.northwestern.edu/stories/2020/03/self-sanitizing-face-mask-project-receives-nsf-rapid-grant, 3 pages (2020).

Park, et al., "Antiviral Properties of Silver Nanoparticles on a Magnetic Hybrid Colloid," Applied and Environmental Microbiology 80(8), pp. 2343-2350 (2014).

Popescu, et al., "Antibacterial efficiency of cellulose-based fibers covered with ZnO and Al2O3 by Atomic Layer Deposition," Applied Surface Science 481, pp. 1287-1298 (2019).

Schieber, "Duke University uses vaporized hydrogen peroxide to clean N95 face masks for reuse," TechCrunch, retrieved from https://techcrunch.com/2020/03/27/duke-university-uses-vaporized-hydrogen-peroxide-to-clean-n95-face-masks-for-reuse, 2 pages (2020).

Te Velthuis, et al., "Zn2 Inhibits Coronavirus and Arterivirus RNA Polymerase Activity In Vitro and Zinc Ionophores Block the Replication of These Viruses in Cell Culture," PLOS Pathogens 6(11), e1001176, 10 pages (2010).

Velasco, et al., "A new role for Zinc limitation in bacterial pathogenicity: modulation of a-hemolysin from uropathogenic *Escherichia coli*," Scientific Report 8, 6535, 11 pages (2018).

\* cited by examiner

|  | Max outgrowth ratio | | | |
| --- | --- | --- | --- | --- |
|  | N95 | N95Jeff | N95Tony | CWR |
| 25 TMo | 0.00 | 0.03 | 0.14 | 0.60 |
| 50cy TW | 0.19 | nd | 0.21 | 0.41 |
| 40cy SMo | 0.37 | 0.75 | 0.64 | 0.24 |
| ZnOMo 15nm | 0.13 | 0.21 | 0.13 | 0.49 |
| ZnTiO 17nm | 0.20 | 0.24 | nd | 0.69 |
| 10nm TiO2 | 1.25 | nd | nd | 0.60 |
| 10nm ZnO | 0.96 | nd | nd | 0.62 |
| AgZnO-20nm | 0.56 | 0.82 | 0.46 | 0.00 |
| AlAgO-10nm | 0.58 | 0.01 | 1.36 | 0.00 |
| AgTiO-20nm | 0.67 | 1.02 | 0.00 | 0.00 |
| AgO-ZnMoO-30nm | 0.02 | 0.03 | 0.00 | 0.00 |

US 11,846,021 B2

ANTIMICROBIAL COATINGS

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates to personal protective equipment. More particularly, the present disclosure relates to systems, methods, and compositions for the formation of antimicrobial coatings on personal protective equipment.

BACKGROUND

Novel materials are being used increasingly in the improvement of health care. The use of personal protective equipment ("PPE") has become increasingly important as the world has faced a viral pandemic. PPE will typically become contaminated during use. Many types of PPE, such as face masks, contain surfaces and environments that can allow microorganisms, including bacteria and viruses, to survive and even reproduce. Many PPE are designed to be a single-use item, where decontamination is not practical.

In particular, PPE masks present a challenge due to their proximity to a user's mouth and nose. The mask is exposed directly to warm, damp openings, such as the nose and mouth, including being in contact with or adjacent to mucous membranes. This environment is ideal for many microbes.

Microorganisms, such as bacteria, fungi, and protozoa, tend to foul any surface where water is present. These microorganisms present a severe threat of fouling due to the ability to reproduce, resulting in growth on the PPE. Viruses present a complex problem as a potential contaminant on PPE due to their small size and general resilience to antibacterial measures, making physical exclusion by filters or removal difficult.

Generally, there are two approaches to combatting microbes that rely on chemical and/or physical interactions with the cells. The physical approach often requires significant structural changes to PPE's existing structure, making those techniques not readily adaptable to existing PPE. In the chemical approach, surface coatings or solutions containing antibiotics, polymers, or metal and metal-oxide (nano)particles (e.g., Cu—, ZnO— and Ag-based) are used. However, use of antibiotics brings a threat of evolving more multi-resistant strains, and additionally, the development of new antibiotics is a very slow and inefficient process. The chemical approach also requires physically locating the chemical(s) on the PPE, which may present a range of challenges. For example, chemical antimicrobial material may not be readily deposited uniformly and/or the deposited material may be easily dislodged once deposited.

SUMMARY

At least one embodiment relates to a method depositing a metal or metal oxide. The deposition proceeds on a base material. The base material is pre-treated with a metal precursor. Then Atomic Layer Deposition or Sequential Infiltration Synthesis is utilized to deposit the metal or metal oxide on the base material. Depositing a metal or metal oxide includes at least one cycle of: pulsing a first metal precursor into the reactor for a first metal precursor pulse time; exposing the base material to the first metal precursor for a first metal precursor exposure time and at a first partial pressure, the first metal precursor binding on or therein with the base material; purging the reactor of the first metal precursor; pulsing a co-reactant precursor into the reactor for a first co-reactant pulse time; exposing the base material to the co-reactant precursor for a co-reactant precursor exposure time and at a second partial pressure, the co-reactant precursor binding on or therein to form the metal or metal oxide; and purging the reactor of the co-reactant precursor.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

FIG. 1A shows 10 nm ZnO CRW, which exhibits no-to-low killing effect. FIG. 1B shows 50cy TW CRW, which exhibits partial killing effect. FIG. 1C shows AgO—ZnMoO-30 nm CRW, which exhibits maximum killing effect.

FIG. 2A shows the control (uncoated CRW) compared to AgZnMo CRW, which exhibits max killing effect. FIG. 2B shows AgZnMo CRW disk compared to AgZnMo CRW culture, which exhibits no diffusion in media. FIG. 2C shows the control (uncoated CRW) compared to AgZnO CRW, which exhibits max killing effect. FIG. 2B shows AgZnO CRW disk compared to AgZnO CRW culture, which exhibits complete diffusion in media.

FIG. 3A shows contact-dependent cell killing by disks coated in AlMo, AlW, Mo, ZnOMo, ZnTiO, $TiO_2$, ZnO, AgZnO, AgAlO, AgTiO, and AgZnMo and an uncoated disk. FIG. 3B shows contact-independent cell killing (e.g., diffusion of coating in growth media) by disks coated in AlMo, AlW, Mo, ZnOMo, ZnTiO, $TiO_2$, ZnO, AgZnO, AgAlO, AgTiO, and AgZnMo and an uncoated disk.

FIG. 4A shows contact-dependent cell killing by disks coated in AlMo, Mo, ZnOMo, ZnTiO, AgZnO, AgAlO, AgTiO, and AgZnMo and an uncoated disk. FIG. 4B shows contact-independent cell killing (e.g., diffusion of coating in growth media) by disks coated in AlMo, Mo, ZnOMo, ZnTiO, AgZnO, AgAlO, AgTiO, and AgZnMo and an uncoated disk.

FIG. 5A shows contact-dependent cell killing by disks coated in AlMo, AlW, Mo, ZnOMo, ZnTiO, AgZnO, AgAlO, AgTiO, and AgZnMo and two uncoated disks. FIG. 5B shows contact-independent cell killing (e.g., diffusion of coating in growth media) by disks coated in AlMo, AlW, Mo, ZnOMo, ZnTiO, AgZnO, AgAlO, AgTiO, and AgZnMo and two uncoated disks.

FIG. 6A shows contact-dependent cell killing by disks coated in AlMo, AlW, Mo, ZnOMo, ZnTiO, $TiO_2$, ZnO, AgZnO, AgAlO, AgTiO, and AgZnMo and two uncoated disks. FIG. 6B shows contact-independent cell killing (e.g., diffusion of coating in growth media) by disks coated in AlMo, AlW, Mo, ZnOMo, ZnTiO, $TiO_2$, ZnO, AgZnO, AgAlO, AgTiO, and AgZnMo and two uncoated disks.

DETAILED DESCRIPTION

Figure 1A:
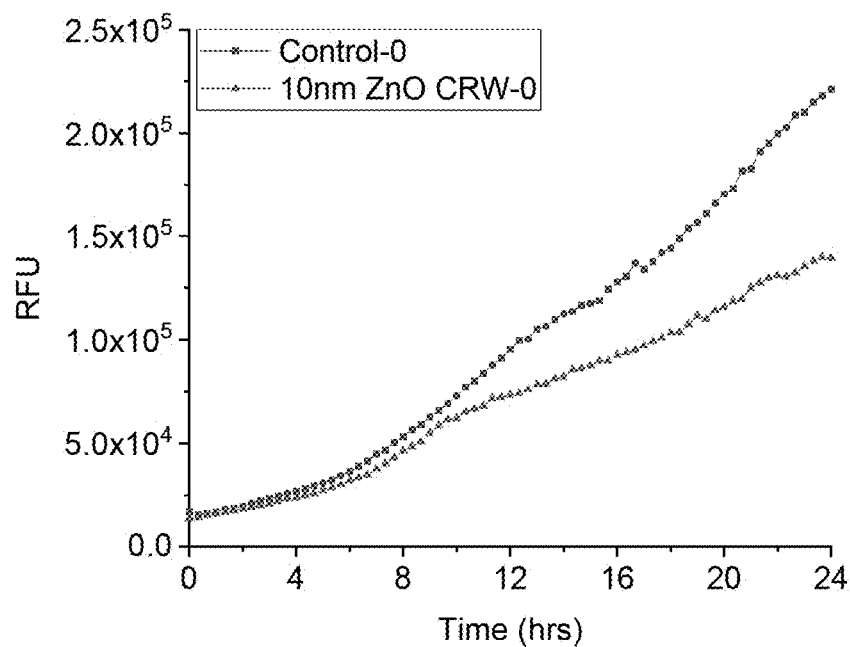
FIGS. 1A-1C show contact-dependent cell killing by coated disks, where each coated disk was compared to a control and the outgrowth of surviving bacteria was monitored.

Certain embodiments relate to atomic layer deposition ("ALD") processes for forming an antimicrobial and/or antiviral material. The antimicrobial and/or antiviral material may be in As used herein, antimicrobial means the property of killing microorganisms such as bacteria and viruses or preventing their growth. As used herein, antibacterial refers to the ability to kill or prevent the growth of bacteria. As used herein, antiviral refers to the ability to render viruses unable to replicate such as demonstrated by a 20% reduction in growth per unit time.

PPE materials have a range of surfaces that may be amenable to deposition or impregnation of antimicrobial materials. However, PPE require a range of physical attributes and performance characteristics that limit the option for such deposition or coating, such as the need for gas permeability, filtration capability and flexibility in PPE masks. Generally PPE, notably masks, are manufactured in "Dry" processALD/SIS can be done "dry"—i.e. no solvent. Other methods for applying antimicrobial coatings use a solvent. The ALD/SIS should be easier to integrate with the PPE manufacturing which is also done dry.

One embodiment relates to ALD. ALD is a conformal, gas-phase deposition process. Each half-reaction proceeds with exposure of gaseous precursors in a sequential, self-limiting process. Each precursor reaction at the surface, allowing deposition on a surface and formation of layers of deposited material.

In an alternative embodiment, sequential infiltration synthesis ("SIS") may be used to deposit and/or impregnate the PPE with antimicrobial material. SIS differs from ALD in that in ALD, precursor vapors react on the surface of polymers; in SIS, the exposure times are much longer to enable diffusion into the polymer free volume, where vapor residence is often further promoted by adduction to polymer functional groups. Thus, while ALD provides a scheme to form layers on a surface, SIS provides a scheme to form materials within a polymer. As used herein, ALD will refer to processes resulting in surface deposition and SIS to processes involving infiltration and deposition within the polymer free volume. ALD/SIS or SIS/ALD refer to processes that result in surface deposition and/or deposition within the polymer free volume.

In one embodiment, each ALD/SIS process consists of a cycle, which may be repeated to form a supercycle, with a first metal precursor vapor pulse for example for 5 seconds, followed by a first metal exposure, for example 30 seconds in a sealed vacuum chamber, followed by a first metal precursor purge, such as 5 seconds, where the reactor is pumped to a vacuum or an inert gas is flushed through the vacuum chamber to remove residual metal precursor and reaction products, followed by a co-reactant pulse (such as water), for example for 2 seconds, with a co-reactant exposure, for example 60 seconds for SIS or 5 seconds for ALD, followed by a co-reactant purge, such as for 120 seconds or an inert gas is flushed through the vacuum chamber to remove residual co-reactant and reaction products. It should be appreciated that more complicated ALD/SIS schemes can be constructed as a supercycle comprising various subcycles for depositing a material as described, such as varying the parameters for any of the individual steps within a cycle.

In one embodiment, the ALD/SIS process is preceded by a precursor exposure step in which the first metal precursor (of an ALD or SIS cycle) or optionally a different metal precursor is introduced into the reaction chamber, such as at a higher pressure and for a longer exposure time compared to the subsequent ALD/SIS cycles. For example, the pre-treatment metal precursor exposure is for at least 6 seconds, such as at least 10-30 seconds, such as about 12-16 seconds. This precursor-soaking step has the effect of chemically priming the substrate surface so that ALD/SIS cycles react to completion.

The described SIS/ALD processes involve the deposition and/or infiltration of a first metal precursor and a co-reactant precursor into a base material and results in the deposition of the respective antimicrobial materials. In one embodiment, the antimicrobial materials are metals or metal oxides. For example, antimicrobial material may include copper (Cu), copper oxide ($Cu_2O$), zinc, zinc oxide (ZnO), titanium dioxide ($TiO_2$), zinc titanium oxide (ZnTiO), molybdenum (Mo), tungsten (W), sliver (Ag), silver oxide (AgO), silver aluminum oxide (AgAlO), silver zinc oxide (AgZnO), molybedenum zinc oxide (MoZnO), aluminum molybdenum oxyfluoride (AlMoOF), and aluminum tungsten oxyfluoride (AlFOW). The composition affects the antibacterial and antiviral properties and can be adjusted to maximize the antibacterial effects, maximize the antiviral effects, or to create a coating which has acceptable levels of antibacterial and antiviral effects. In particular, stoichiometric variations are envisioned as a consequence of the duration of vapor exposure and purge. Further, stoichiometric variations can be achieved by the use of different co-reactant precursors.

In addition, it should be appreciated that dopants may added between cycles of depositing the antimicrobial metals. For example, material can be doped directly through the SIS process by substituting the first metal precursor for one or more cycles with an appropriate dopant precursor and the doping level could conceivably be controlled with the exposure of dopant precursor and purge time.

The base material may be selected from polymers. For example, in one embodiment the base material is a polymer having a Lewis basic function group. The base material is preferably free of residual materials, such as solvents, that are reactive with the precursors, such as the first metal precursor and the co-reactant precursor. In certain embodiments, the base material may contain polypropylene, polyethylene, polyester, polysulfone, polyethersulfone, polyurethane, polyvinylidene fluoride, polytetrafluoroethylene. Polypropylene, polyethylene and polyester are common polymer materials used to manufacture the filter element in N95 masks used as PPE. The polypropylene, polyethylene and polyester used as filter elements in N95 masks are typically electret treated to impart an electrostatic charge. This electrostatic charge is instrumental in preventing small particles from passing through the mask and achieving a high filtration efficiency. Any antimicrobial coating treatment must preserve the filtration efficiency or the N95 filter will no longer be effective.

In some embodiments, the first metal precursor vapor pulse comprises input to the reactor of the first metal precursor vapor for a first metal precursor vapor pulse time of 0.5 seconds to 30 seconds (e.g., 0.5, 1, 5, 10, 20, 30 seconds, inclusive of all ranges and values therebetween), such as 0.5 to 5 seconds for ALD in one embodiment and 10 to 30 seconds for SIS in another embodiment. The first partial pressure of the first metal precursor vapor pulse can be in the range of 0.01 Torr to 1,000 Torr (e.g., 10, 25, 50, 75, 100, 500, 1000 Torr, inclusive of all ranges and values therebetween), in one embodiment for SIS at least 50 Torr and in a pressurized reactor embodiment at least 1000 Torr. One of skill in the art will appreciate that the time length, pressure, and amount of precursor for the pulse are all factors in determining the overall amount for each of those operation parameters. For example, the pressure and amount may follow from the duration of the pulse but depend on the size of the chamber and the type of valve as would be understood from general knowledge regarding ALD and SIS reactions. Note, for ease of reference herein the process is described with regard to the pulse duration but it is understood that the product of pulse duration and precursor partial pressure is what dictates the precursor exposure and must be sufficiently high to ensure saturation. In one embodiment, the precursor pulse durations of 2-4 seconds are used for the ALD/SIS and longer precursor pulse durations of 12-16 seconds for the precursor soaking step prior to the ALD/SIS.

In some embodiments, the first metal precursor exposure comprises exposing the base material to the first metal precursor for a first metal exposure time and a first partial pressure of the first metal precursor so that the first metal precursor infiltrates at least a portion of the base material (e.g., infiltrates beneath the surface) and binds with the base material. The first metal exposure time can be in the range of 0.5 seconds to 500 seconds (e.g., 0.5, 1, 5, 10, 20, 30, 40, 50, 60, 70, 80, 90, 100, 120, 140, 160, 180, 200, 220, 240, 260, 280, 300, 350, 400, 450 or 500 seconds, inclusive of all ranges and values therebetween). In some embodiments, the first predetermined time is in the range of 1 and 10 seconds, for example about 5 seconds. The first partial pressure of the first metal precursor can be in the range of 0.01 Torr to 1000 Torr (e.g., 0.01, 0.05, 0.1, 0.5, 1.0, 5.0, 10 Torr, inclusive of all ranges and values therebetween). In some embodiments, the first partial pressure of the first metal precursor is in the range of 0.1 Torr and 1 Torr, for example about 0.5 Torr. In one embodiment, the ALD/SIS coatings were prepared in a continuous flow mode where the valve to the vacuum pump was open all the time and the precursors were injected into a constant flow of inert carrier gas. In this case the precursor vapor pulse time and the precursor exposure time were not separate steps but were executed concurrently. In one embodiment, precursor pulse durations are of 2-4 seconds for the ALD/SIS and longer precursor pulse durations of 12-16 seconds for the precursor soaking step prior to the ALD/SIS.

The first metal precursor purge evacuates unreacted precursor from the reactor. The first metal precursor purge may be for a first metal precursor purge time of 0.5 seconds to 500 seconds (e.g., 0.5, 1, 5, 10, 20, 30, 40, 50, 60, 70, 80, 90, 100, 120, 140, 160, 180, 200, 220, 240, 260, 280, 300, 350, 400, 450 or 500 seconds, inclusive of all ranges and values therebetween), such as 30 seconds. The first metal precursor purge reduces the pressure in the reactor to within the range of 0.01 Torr to 10 Torr (e.g., 0.01, 0.05, 0.1, 0.5, 1.0, 5.0, 10 Torr, inclusive of all ranges and values therebetween), such as substantially to vacuum in systems where the vacuum chamber is evacuated during the precursor purge step. In continuous flow systems, the inert carrier gas flow is maintained during the purge steps and the pressure in the reactor reduces to the steady-state pressure dictated by the carrier gas mass flow rate. In the one embodiment, where continuous flow operation was performed, the steady state reactor pressure was ~1 Torr, and the duration of the precursor purge was 30 seconds.

In some embodiments, the base material can be heated to a predetermined temperature during the SIS process. For example, the first predetermined temperature can be in the range of 30-200° C. (e.g., 30, 40, 50, 60, 70, 80, 90, 100, 110, 120, 130, 140, 150, 160, 170, 180, 190 or 200° C., inclusive of all ranges and values therebetween). In some embodiments, the predetermined temperature is in the range of 50-60° C., for example 60° C. In some embodiments, the first predetermined temperature can be in the range of 120-140° C., for example 135° C. Temperature also impacts the overall energy in the system and the performance for diffusion and/or reaction. In some embodiments, low temperatures of 50-60° C. which are substantially lower than the standard temperatures of ~200° C. for ALD and ~120° C. for SIS are used. These low temperatures were used for coating the PPE materials because higher temperatures were found to degrade the PPE materials.

In some embodiments, first metal precursor includes, for example, trimethyl aluminum, titanium tetrachloride, diethyl zinc, tungsten hexafluoride, molybdenum hexafluoride, silver hexafluoroacetylacetonate trimethylphosphine adduct, and copper amidinate. For the ALD/SIS on the PPE materials requiring low deposition temperatures, the first metal precursor must have a relatively high vapor pressure of at least ~0.1 Torr at the deposition temperature. If the vapor pressure of the first metal precursor is substantially below ~0.1 Torr at the deposition temperature, the precursor pulse times and exposure times will become excessively long and the ALD/SIS processing will not be practical. In addition, the first metal precursor must have a relatively high reactivity on the PPE material and on the SIS/ALD film material such that the reactive sticking coefficient is at least ~$10^{4}$ at the deposition temperature. If the reactive sticking coefficient of the first metal precursor is substantially below ~$10^{-4}$ at the deposition temperature, the precursor pulse times and exposure times will become excessively long and the precursor will not be efficiently utilized and the ALD/SIS processing will not be practical.

The base material, after reaction with the first metal precursor, is then exposed to a second precursor—the co-reactant precursor—by a co-reactant pulse introducing the co-reactant to the reactor and then exposing for the co-reactant exposure such that the second co-reactant precursor reacts with the first metal precursor to form the inorganic material on or within the base material. In some embodiments, the first co-reactant precursor may include one or more of water, hydrogen peroxide, and ozone. Note, varying the co-reactant may also vary the stoichiometry of the resultant oxide coating. Further precursors may include disilane, ammonia, trimethyl aluminum, diethyl zinc, formaldehyde, hydrogen, formic acid, and combinations of these chemicals supplied either concurrently or in sequence.

In some embodiments, the first metal precursor vapor pulse comprises input to the reactor of the first metal precursor vapor for a co-reactant precursor pulse time of 0.5 seconds to 500 seconds (e.g., 0.5, 1, 5, 10, 20, 30, 40, 50, 60, 70, 80, 90, 100, 120, 140, 160, 180, 200, 220, 240, 260, 280, 300, 350, 400, 450 or 500 seconds, inclusive of all ranges and values therebetween), such as 2 seconds. The first partial pressure of the co-reactant precursor pulse can be in the range of 0.01 Torr to 100 Torr (e.g., 0.01, 0.05, 0.1, 0.5, 1.0, 5.0, 10, 50, 100 Torr, inclusive of all ranges and values therebetween).

In some embodiments, exposing the base material to the co-reactant precursor for a co-reactant precursor exposure time and a second partial pressure of the co-reactant precursor so that the co-reactant precursor infiltrates at least a portion of the base material (e.g., infiltrates beneath the surface) and reacts with the moiety formed by the first metal precursor reacting with the base material. The co-reactant precursor exposure time can be in the range of 0.5 seconds to 500 seconds (e.g., 0.5, 1, 5, 10, 20, 30, 40, 50, 60, 70, 80, 90, 100, 120, 140, 160, 180, 200, 220, 240, 260, 280, 300, 350, 400, 450 or 500 seconds, inclusive of all ranges and values therebetween), for example about 60 seconds. The second partial pressure of the co-reactant precursor can be in the range of 0.01 Torr to 100 Torr (e.g., 0.01, 0.05, 0.1, 0.5, 1.0, 5.0, 10, 50, 100 Torr, inclusive of all ranges and values therebetween). In some embodiments, the second partial pressure of the co-reactant precursor is in the range of 0.1 Torr and 1 Torr, for example about 0.5 Torr.

The co-reactant precursor purge evacuates unreacted precursor from the reactor. The co-reactant precursor purge may be for a co-reactant precursor purge time of 0.5 seconds to 500 seconds (0.5, 1, 5, 10, 20, 30, 40, 50, 60, 70, 80, 90, 100, 120, 140, 160, 180, 200, 220, 240, 260, 280, 300, 350, 400, 450 or 500 seconds, inclusive of all ranges and values therebetween), such as 120 seconds. The co-reactant precursor purge reduces the pressure in the reactor to within the range of 0.01 Torr to 10 Torr (e.g., 0.01, 0.05, 0.1, 0.5, 1.0, 5.0, 10 Torr, inclusive of all ranges and values therebetween), such as substantially to vacuum in systems where the vacuum chamber is evacuated during the precursor purge step. In continuous flow systems, the inert carrier gas flow is maintained during the purge steps and the pressure in the reactor reduces to the steady-state pressure dictated by the carrier gas mass flow rate. In some embodiments, where continuous flow operation was performed, the steady state reactor pressure was ~1 Torr, and the duration of the precursor purge was 30 seconds.

In some embodiments, the second co-reactant precursor may include one or more of water, hydrogen peroxide, and ozone. Note, varying the co-reactant may also vary the stoichiometry of the resultant oxide coating. Further precursors may include nitrous oxide, hydrogen, formaldehyde, trimethyl aluminum, ammonia, hydrazine, dimethyl hydrazine, diethyl hydrazine, methyl-ethyl hydrazine, hydrogen sulfide, trimethyl phosphite, trimethyl phosphate, silane, disilane, or any combination thereof supplied either concurrently or in sequence.

Any number of cycles of exposing the base material to the first metal precursor and the second co-reactant precursor can be performed to reach a depth within the base material that the inorganic material has infiltrated as well as amount of inorganic material deposited therein. In some embodiments, the number of cycles of the ALD/SIS process can be in the range of 1-500 (e.g., 1 cycle, 2, 3, 4, 5, 10, 15, 20, 25, 30, 35, 40, 45, 50, 100, 200, 300, 400, or 500 cycles, inclusive of all ranges and values therebetween). In some embodiments, up to 10 cycles of the ALD/SIS process provide for linear growth and are used to form a desired thickness of the inorganic material on the base material.

In general, the SIS process involves exposing the base material, which can be formed from an organic material, to various gas phase precursors (e.g., the first metal precursor and the second co-reactant precursor) to synthesize the inorganic material, similar to ALD. However, contrary to other deposition methods, such as ALD, which only forms the inorganic material on a surface of the substrate, SIS coats the surface of the substrate but also infiltrates into the bulk substrate. This is achieved by adjusting the partial pressure and time of the gas phase precursor exposures (i.e., the first metal precursor and the second co-reactant precursor). In some embodiments, the total time of exposure to first metal precursor and/or the second co-reactant precursor during SIS cycle may be 5-1000 times higher, and the partial pressures may be 5-10,000 times larger than the typical time and partial pressure for an ALD cycle.

In some embodiments, the SIS process may include relatively long periods of gas phase exposure and high partial pressure of the first metal precursor and the second co-reactant precursor. For example, the SIS method may include a relatively long period of gas phase exposure and high partial pressure of the first metal precursor followed by a long period of exposure and high partial pressure of the second co-reactant precursor. In various embodiments, a purging step can be performed in-between exposure to the first metal precursor and the second co-reactant precursor. With regard to ALD, a main differentiation is in the purge time after the metal precursor dose.

For example, the base material can be positioned in a hermetically sealed chamber pumped to vacuum. The base material is exposed to the first metal precursor for the first predetermined time (e.g., between 1 second and 500 seconds) and the first partial pressure (e.g., between 0.01 Torr and 10 Torr). The chamber is then evacuated and/or purged with an inert gas (e.g., nitrogen, argon, or any other inert gas) before exposing the base material to the second co-reactant component. In another embodiment, the method may include a series of short pulses of the first metal precursor followed by another series of short pulses of the second co-reactant precursor. In some embodiments, a series of short pulses may be combined with long periods of gas phase exposure to the first metal precursor and/or the second co-reactant precursor.

In SIS embodiments, the first metal precursor infiltrates within the base material and selectively binds (either covalently or non-covalently) to a functional group of the base material (e.g., a carbonyl group). The second co-reactant precursor is selectively reactive with the first metal precursor that is bound to the base material. In some embodiments, a third precursor may be used. For example, a dopant can be deposited either as less than a single atomic layer (ad-islands or particles) or as a dopant layer, such as to alter conductivity or magnetic properties.

The SIS process results in the growth of the inorganic material in a sub-surface region of the base material associated with the first metal precursor and the second co-reactant precursor used as well as, in some embodiments, on the surface of the base material. In some ALD embodiments, the inorganic material can form an inorganic layer that may have a thickness in the range of 0.2 nm to 5,000 nm. In some embodiments, the inorganic material can infiltrate the base material via SIS so as to infuse the base material polymer with the inorganic material to a depth of 2 nm to 100 nm. Repeated ALD or SIS cycles will result in thicker layers. In one embodiment, the deposited layers are 10-30 nm or may be selected in terms of cycles, such as 10-100 cycles, for example 30-50 cycles.

One of skill in the art will appreciate that the SIS parameters described herein may be varied based on the overall reaction parameters. For example, high temperatures (above 95° C., such as up to 150° C., could be utilized if the reactor was engineered to quickly remove excess metal precursor such that water could then be quickly introduced (i.e., minimal pumping/purging time) in order to capture/quench the adduct before it (more) quickly dissociates at high temp. Further, temperatures below 80° C., such as down to 60° C. or down to room temperature, could be utilized in some embodiments.

Experimental Results and Analysis.

TABLE 1a

Example coating ALD recipes

| Coating ID | Precursors | ALD Cycles | Precursor Soaking | ALD Timing(s) |
|---|---|---|---|---|
| ZnO | DEZ, $H_2O$ | 70 | DEZ/12 s | DEZ, $H_2O$: 4-30-2-30 |
| $TiO_2$ | $TiCl_4$, $H_2O$ | 100 | $TiC_4$/12 s | $TiCl_4$, $H_2O$: 4-30-2-30 |
| ZnTiO | DEZ, $TiCl_4$, $H_2O$ | 10 (3x ZnO + 5x TiO) | DEZ/16 s | DEZ, $H_2O$: 4-30-2-30 $TiCl_4$, $H_2O$: 4-30-2-30 |
| AlW | TMA, $WF_6$ | 50 | TMA/12 s | TMA, $WF_6$: 4-30-3-30 |
| AlMo | TMA, $MoF_6$ | 25 | TMA/12 s | TMA, $MoF_6$: 4-30-3-30 |
| Mo | $Si_2H_6$, $MoF_6$ | 40 | TMA/12 s | $Si_2H_6$, $MoF_6$: 4-30-4-30 |
| ZnOMo | DEZ, $H_2O$, $MoF_6$ | 11 (3x ZnO + 2x $MoF_6$-DEZ) | DEZ/16 s | DEZ, $H_2O$: 4-30-2-30 $MoF_6$, DEZ: 4-30-2-30 |
| AgAlO | Ag(hfac)$Pme_3$, TMA, $H_2O$ | 30 (1x AlO + 2x AgO) | TMA/12 s | TMA, $H_2O$: 4-30-2-30 Ag, $H_2O$: 20-30-2-30 |
| AgZnO | Ag(hfac)$Pme_3$, DEZ, $H_2O$ | 30 (1x ZnO + 2x AgO) | DEZ/12 s | DEZ, $H_2O$: 4-30-2-30 Ag, $H_2O$: 20-30-2-30 |
| AgTiO | Ag(hfac)$Pme_3$, $TiCl_4$, $H_2O$ | 25 (1x ZnO + 3x AgO) | $TiC_4$/12 s | $TiCl_4$, $H_2O$: 4-30-2-30 |
| AgZnMo | Ag(hfac)$Pme_3$, $H_2O$, DEZ, $MoF_6$ | 30 [2x($H_2O$—Ag) + 1x($MoF_6$-DEZ)] | DEZ/12 s | $MoF_6$, DEZ: 4-30-4-30 $H_2O$, Ag: 2-30-20-30 |

TABLE 1b

Example coating ALD conditions

| Coating ID | Deposition T (° C.) | Bubbler T (° C.) | Bubbler Flow (sscm) | Total Flow (sscm) | Base Pressure (Torr) | Ellipsometry Thickness (nm) | Notes |
|---|---|---|---|---|---|---|---|
| ZnO | 50 | N/A | N/A | 75 | 0.5 | 10 | Colorless deposit |
| $TiO_2$ | 50 | N/A | N/A | 75 | 0.5 | 10 | Colorless deposit |
| ZnTiO | 50 | N/A | N/A | 75 | 0.5 | 17 | Colorless deposit |
| AlW | 50 | N/A | N/A | 75 | 0.5 | 18 | Light gray deposit |

TABLE 1b-continued

Example coating ALD conditions

| Coating ID | Deposition T (° C.) | Bubbler T (° C.) | Bubbler Flow (sscm) | Total Flow (sscm) | Base Pressure (Torr) | Ellipsometry Thickness (nm) | Notes |
|---|---|---|---|---|---|---|---|
| AlMo | 50 | N/A | N/A | 75 | 0.5 | 23 | Light brown deposit |
| Mo | 50 | N/A | N/A | 75 | 0.5 | Not measurable | Growth on outlet side only |
| ZnOMo | 50 | N/A | N/A | 75 | 0.5 | 15 | Light brown deposit |
| AgAlO | 60 | 60 | 60 | 120 | 0.65 | 10 | Light yellow deposit Outlet side less yellow |
| AgZnO | 60 | 60 | 60 | 120 | 0.65 | 20 | Yellow deposit |
| AgTiO | 60 | 60 | 60 | 120 | 0.65 | 20 | Light yellow deposit |
| AgZnMo | 60 | 60 | 60 | 120 | 0.65 | 30 | Dark brown deposit |

Experiments on depositions of the materials listed in Table 1a-1b demonstrated that the above ALD processes resulted in deposition of the intended material within the base material. Testing was done on clean room wipes ("CRW"), using Choice 700 branded polyester wipes, moldex 2310 N99 masks ("Tony") with a polypropylene filter and liner and a polyethylene shell, the valve is natural rubber and polystyrene, a 3M 1860 N95 mask ("Jeff") with a polypropylene filter and polyester shell, and a N95 mask sold by Kimberly-Clark as 46727 N95 ("N95") which has polypropylene filters. Antimicrobial testing.

Experiments using contact dependent cell killing were performed suing a disk-in-well setup. E. coli were used as the example bacteria. Each coated disk was compared to an uncoated control for grow of bacteria.

Figure 1B:
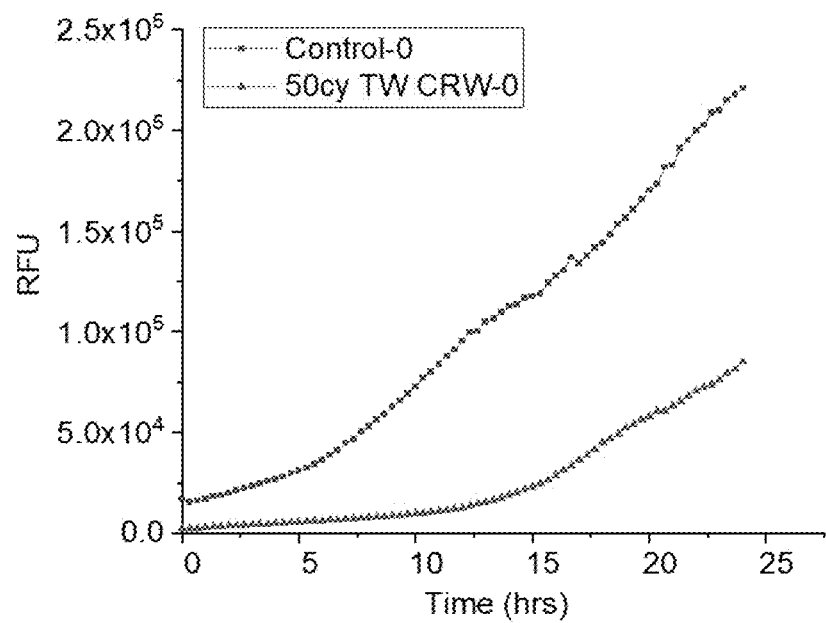
Figure 1C:
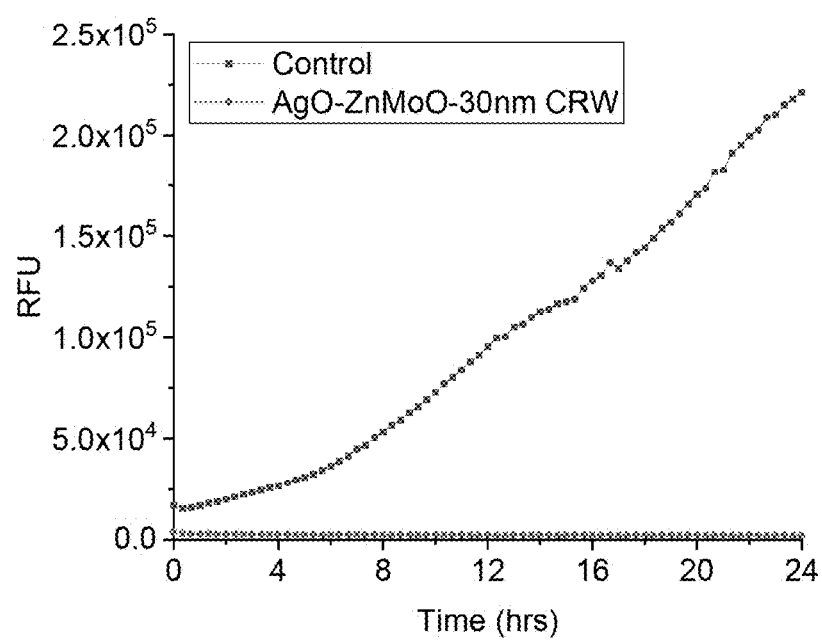

FIGS. 1A-1C show contact-dependent cell killing by coated disks, where each coated disk was compared to a control and the outgrowth of surviving bacteria was monitored. FIG. 1A shows 10 nm ZnO CRW, which exhibits no-to-low killing effect. FIG. 1B shows 50cy TW CRW, which exhibits partial killing effect. FIG. 1C shows AgO—ZnMoO-30 nm CRW, which exhibits maximum killing effect.

Figure 2A:
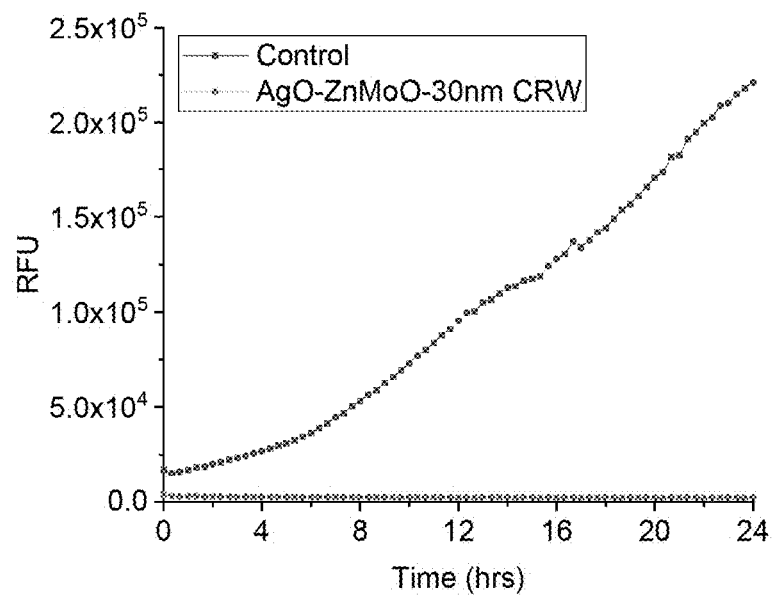
FIGS. 2A-2D show contact-independent cell killing from potential diffusion of coating in growth media, where each coated disk was compared to a control and the bacteria cell mass was monitored (cells were added in media).
Figure 2B:
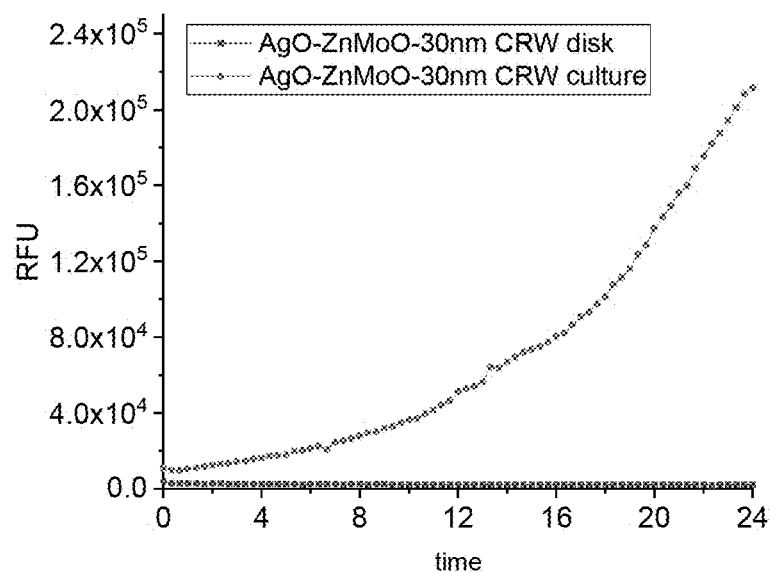
Figure 2C:
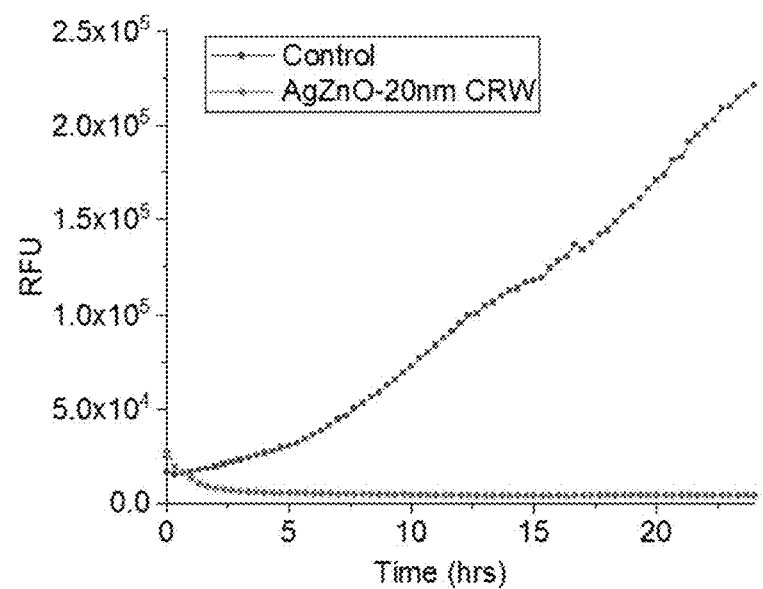
Figure 2D:
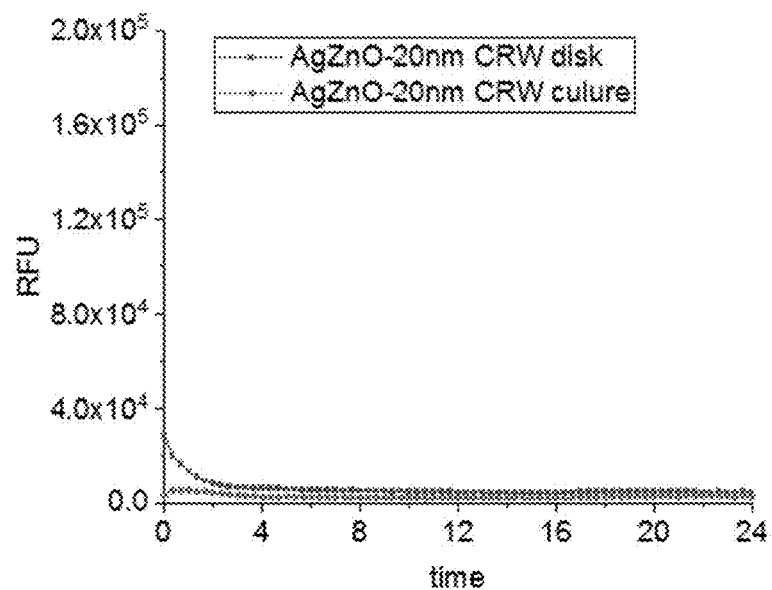

FIGS. 2A-2D show contact-independent cell killing from potential diffusion of coating in growth media, where each coated disk was compared to a control and the bacteria cell mass was monitored (cells were added in media). FIG. 2A shows the control (uncoated CRW) compared to AgZnMo CRW, which exhibits max killing effect. FIG. 2B shows AgZnMo CRW disk compared to AgZnMo CRW culture, which exhibits no diffusion in media. FIG. 2C shows the control (uncoated CRW) compared to AgZnO CRW, which exhibits max killing effect. FIG. 2B shows AgZnO CRW disk compared to AgZnO CRW culture, which exhibits complete diffusion in media.

Figure 3A:
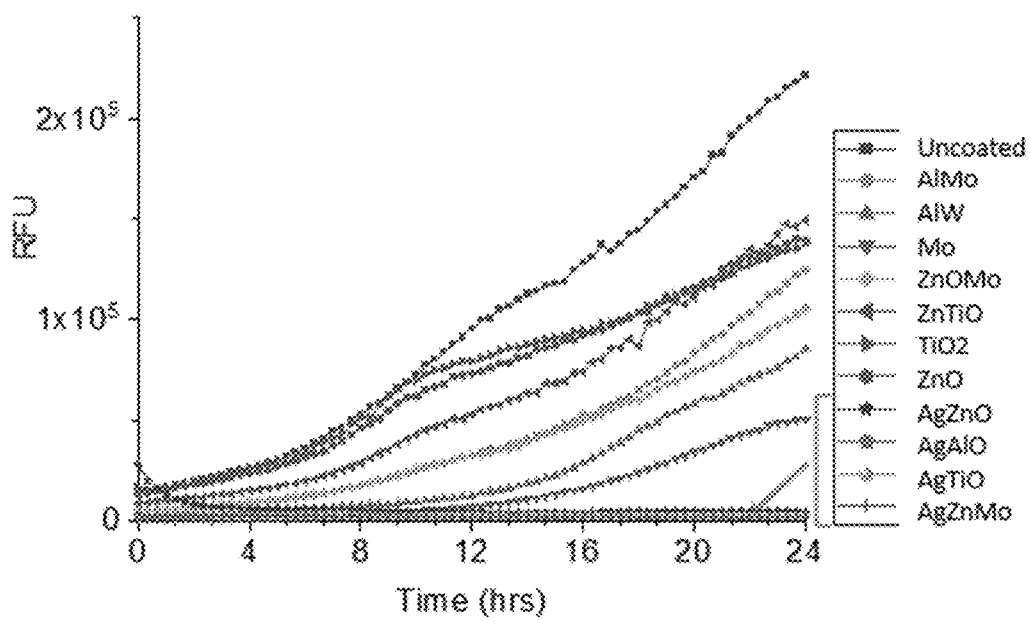
FIGS. 3A-3B show results from the CWR series.
Figure 3B:
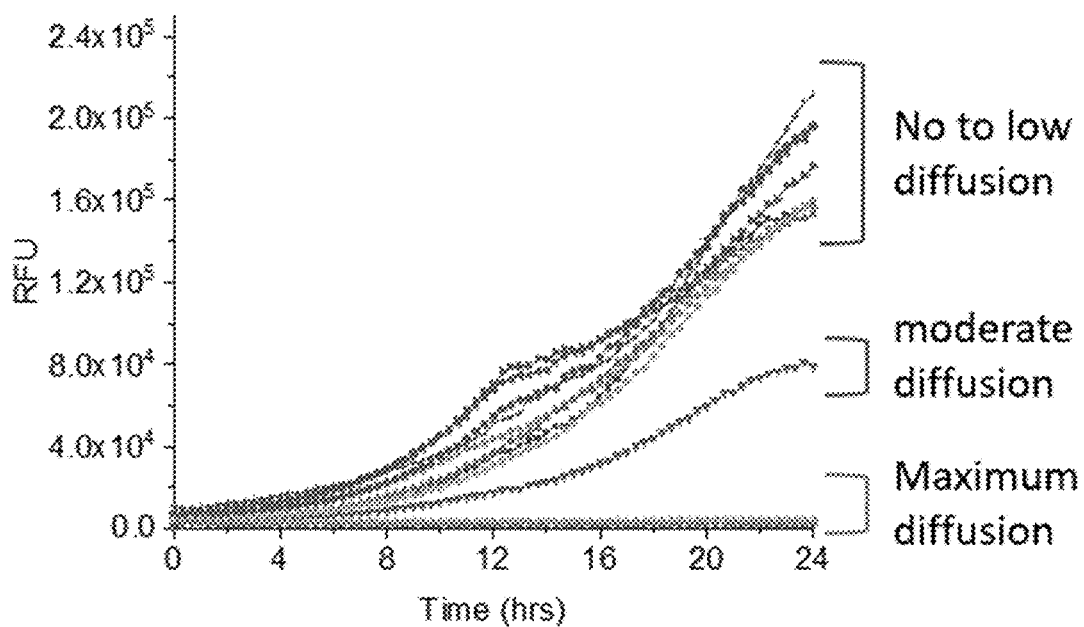

FIGS. 3A-3B show results from the CWR series. FIG. 3A shows contact-dependent cell killing by disks coated in AlMo, AlW, Mo, ZnOMo, ZnTiO, TiO$_2$, ZnO, AgZnO, AgAlO, AgTiO, and AgZnMo and an uncoated disk. FIG. 3B shows contact-independent cell killing (e.g., diffusion of coating in growth media) by disks coated in AlMo, AlW, Mo, ZnOMo, ZnTiO, TiO$_2$, ZnO, AgZnO, AgAlO, AgTiO, and AgZnMo and an uncoated disk.

Figure 4A:
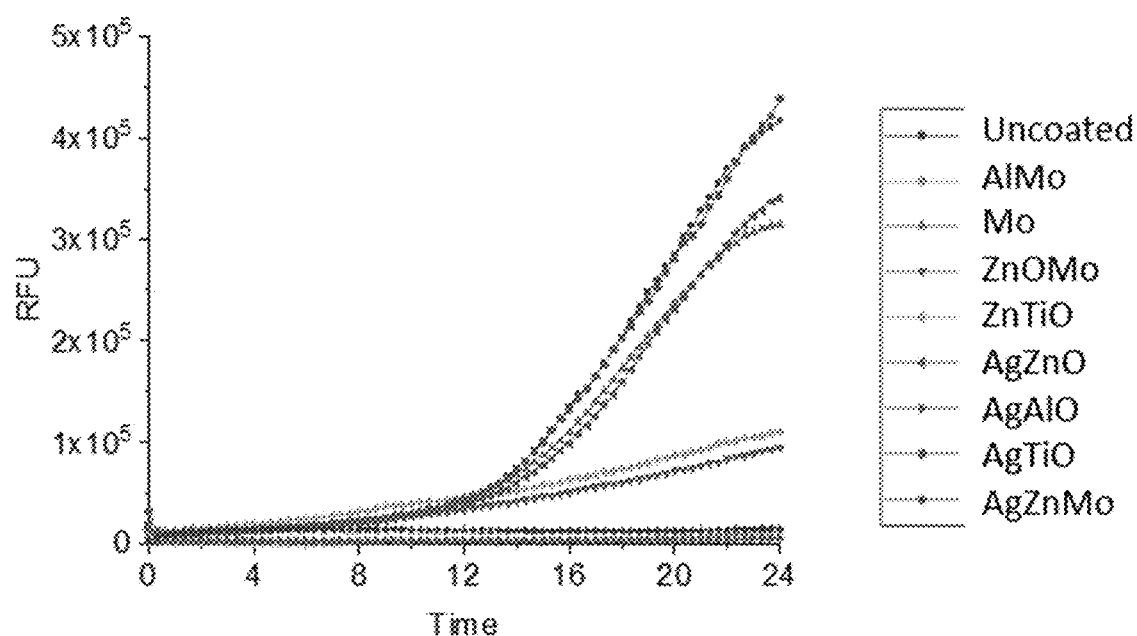
FIGS. 4A-4B show results from the Jeff series.
Figure 4B:
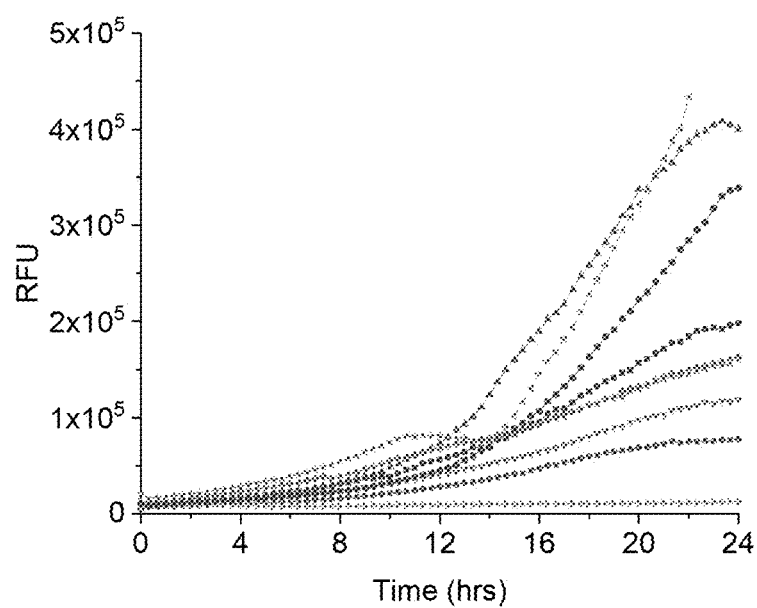

FIGS. 4A-4B show results from the Jeff series. FIG. 4A shows contact-dependent cell killing by disks coated in AlMo, Mo, ZnOMo, ZnTiO, AgZnO, AgAlO, AgTiO, and AgZnMo and an uncoated disk. FIG. 4B shows contact-independent cell killing (e.g., diffusion of coating in growth media) by disks coated in AlMo, Mo, ZnOMo, ZnTiO, AgZnO, AgAlO, AgTiO, and AgZnMo and an uncoated disk.

Figure 5A:
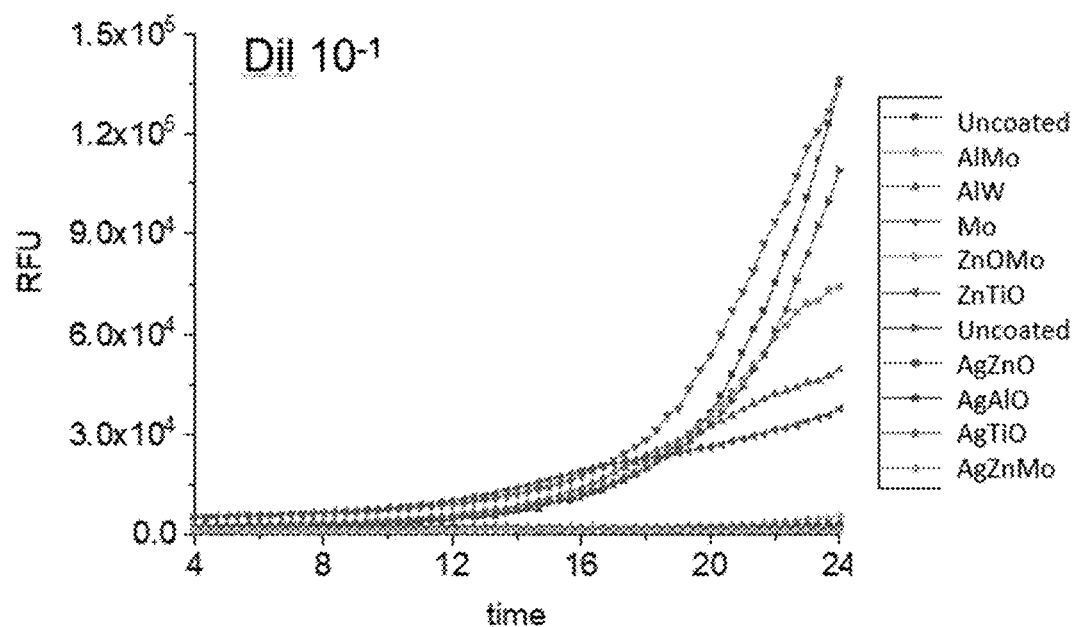
FIGS. 5A-5B show results from the Tony series.
Figure 5B:
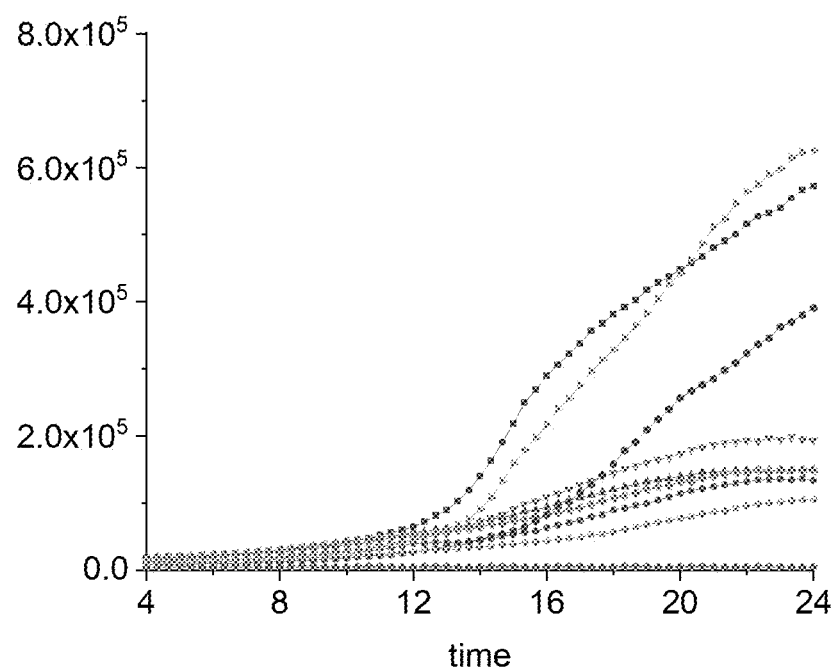

FIGS. 5A-5B show results from the Tony series. FIG. 5A shows contact-dependent cell killing by disks coated in AlMo, AlW, Mo, ZnOMo, ZnTiO, AgZnO, AgAlO, AgTiO, and AgZnMo and two uncoated disks. FIG. 5B shows contact-independent cell killing (e.g., diffusion of coating in growth media) by disks coated in AlMo, AlW, Mo, ZnOMo, ZnTiO, AgZnO, AgAlO, AgTiO, and AgZnMo and two uncoated disks.

Figure 6A:
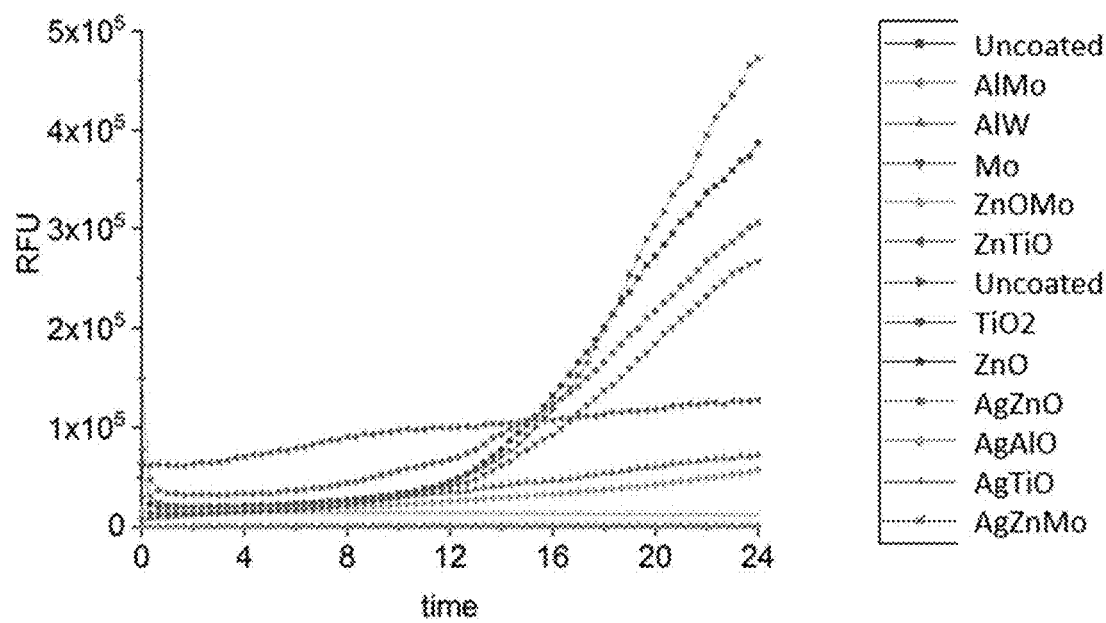
FIGS. 6A-6B show results from the N95 series.
Figure 6B:
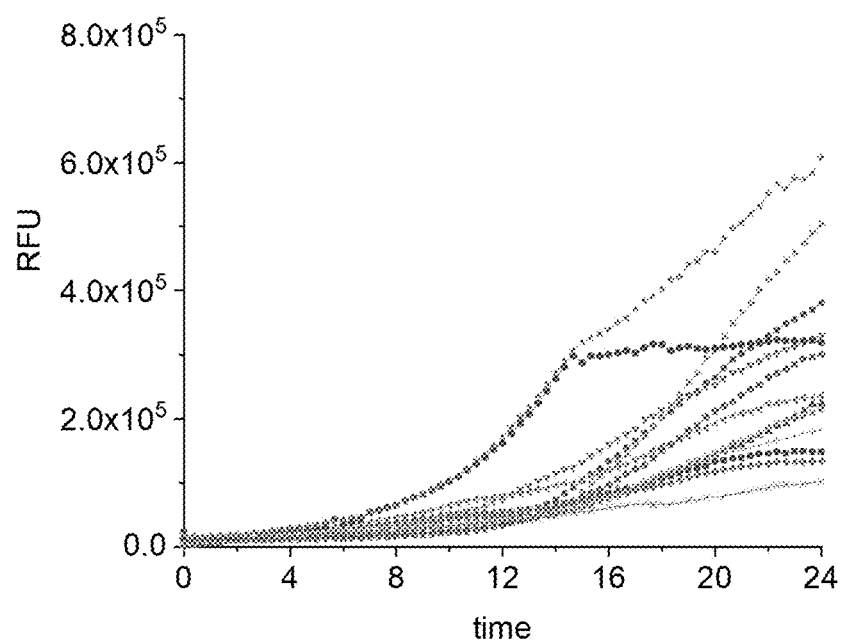

FIGS. 6A-6B show results from the N95 series. FIG. 6A shows contact-dependent cell killing by disks coated in AlMo, AlW, Mo, ZnOMo, ZnTiO, TiO$_2$, ZnO, AgZnO, AgAlO, AgTiO, and AgZnMo and two uncoated disks. FIG. 6B shows contact-independent cell killing (e.g., diffusion of coating in growth media) by disks coated in AlMo, AlW, Mo, ZnOMo, ZnTiO, TiO$_2$, ZnO, AgZnO, AgAlO, AgTiO, and AgZnMo and two uncoated disks.

Figure 7A:
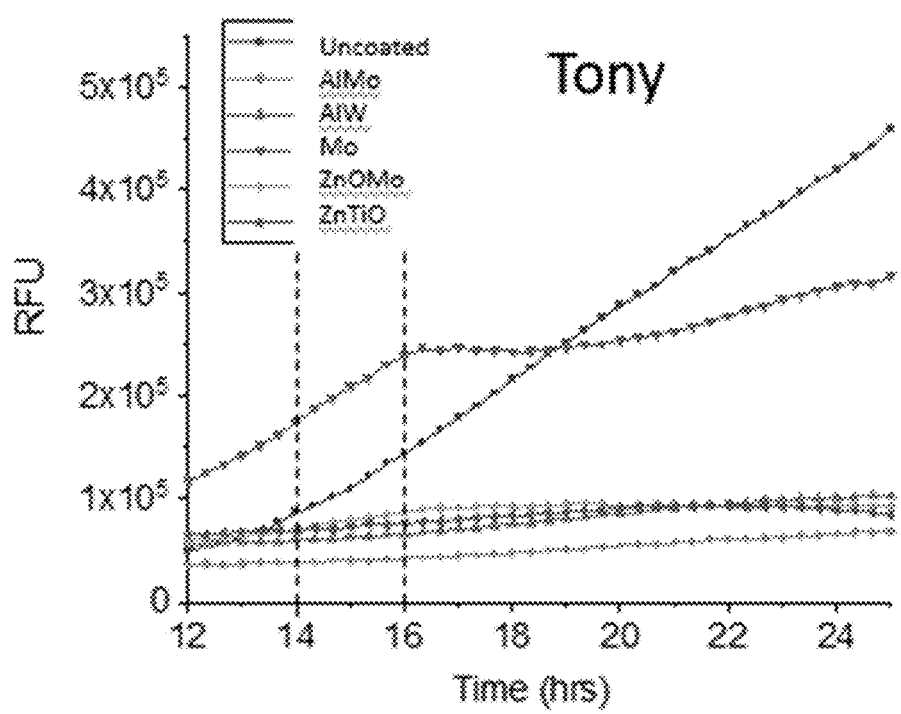
FIG. 7A shows contact-(dependent cell killing by disks from the Tony series coated in AlMo, AlW, Mo, ZnOMo, and ZnTiO and an uncoated disk.
Figure 7B:
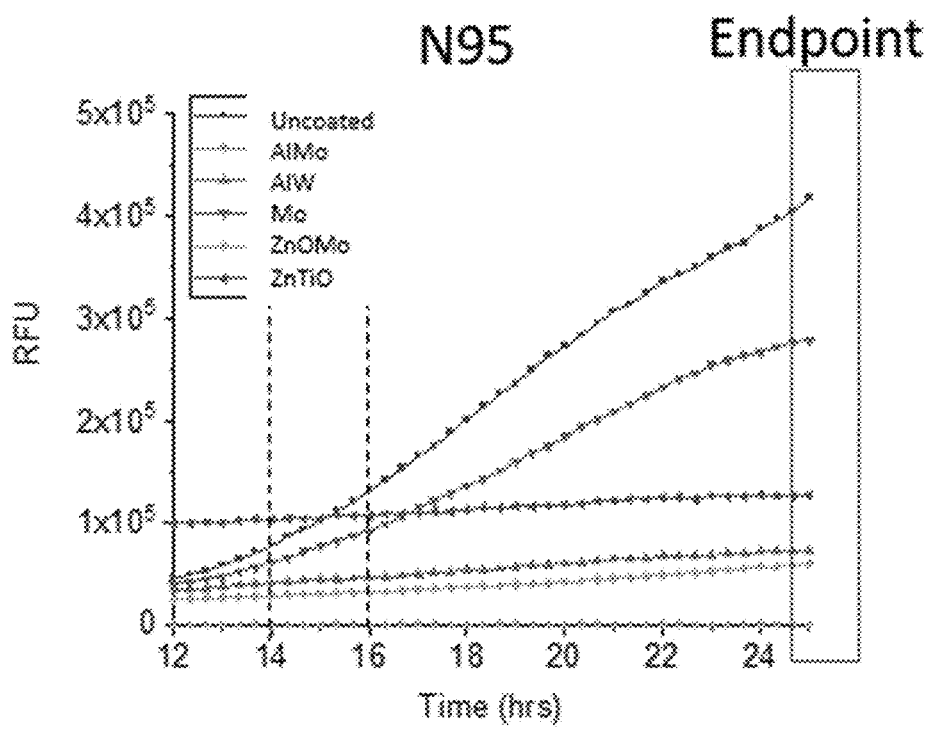
FIG. 7B shows contact-dependent cell killing by disks from the N95 series coated in AlMo, AlW, Mo, ZnOMo, and ZnTiO and an uncoated disk.
Figures 7C, 7D:
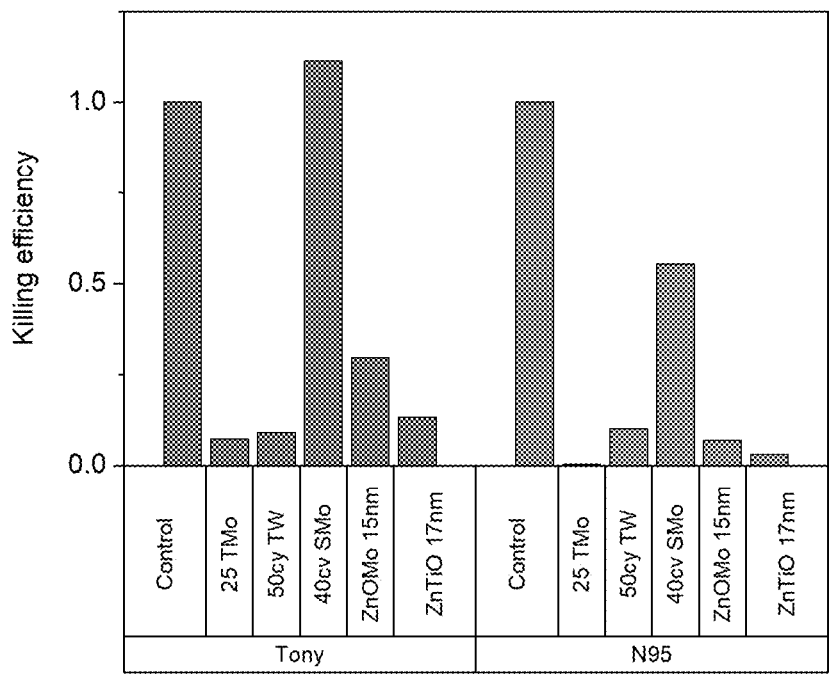
FIGS. 7C-7D are a bar graph (FIG. 7C) and table (FIG. 7D) comparing the killing efficiency the disks shown in FIGS. 7A and 7B.

FIG. 7A shows contact-(dependent cell killing by disks from the Tony series coated in AlMo, AlW, Mo, ZnOMo, and ZnTiO and an uncoated disk. FIG. 7B shows contact-dependent cell killing by disks from the N95 series coated in AlMo, AlW, Mo, ZnOMo, and ZnTiO and an uncoated disk. FIGS. 7C-7D are a bar graph (FIG. 7C) and table (FIG. 7D) comparing the killing efficiency the disks shown in FIGS. 7A and 7B.

Antiviral Testing

Experimental testing was done using a surrogate virus (PhiX174) to test PPE performance as a barrier. Results were evaluated in terms of multiplicity of infection "MOI" as a ratio of virons per cell and in terms of a phage recovery assay. In a first experimental approach, serial dilution of phages is applied to several test disks; phages where recovered and 1/10 of the total volume is used to infect cell culture. In a second experimental approach, phage is applied (no dilution), recovered and then serially diluted prior to infect cell culture. Both approaches exhibited similar results, with OD as function of MOI, at a given time after infection and OD as a function of time, at a given MOI.

Figures 8A, 8B:
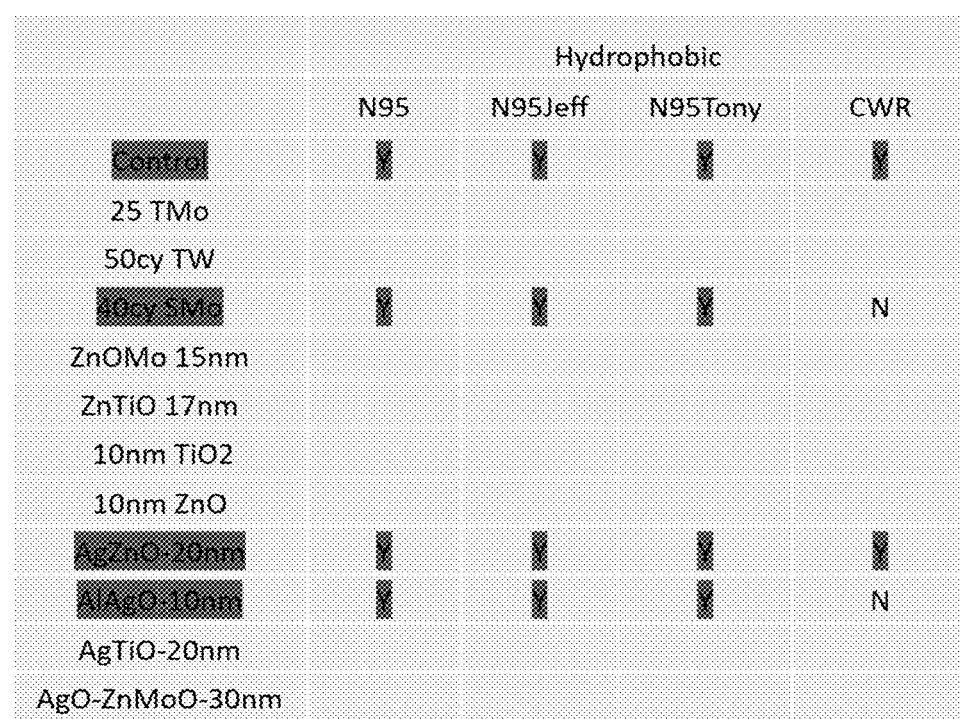
FIG. 8A shows the max outgrowth ratio for the N95, Jeff, Tony, and CWR series for disks coated in the indicated materials.
FIG. 8B shows whether the N95, Jeff, Tony, and CWR series for disks coated in the indicated materials are hydrophobic, where no entry indicates not hydrophobic.

FIG. 8A shows the max outgrowth ratio for the N95, Jeff, Tony, and CWR series for disks coated in the indicated materials. FIG. 8B shows whether the N95, Jeff, Tony, and CWR series for disks coated in the indicated materials are hydrophobic, where no entry indicates not hydrophobic.

Figure 9:
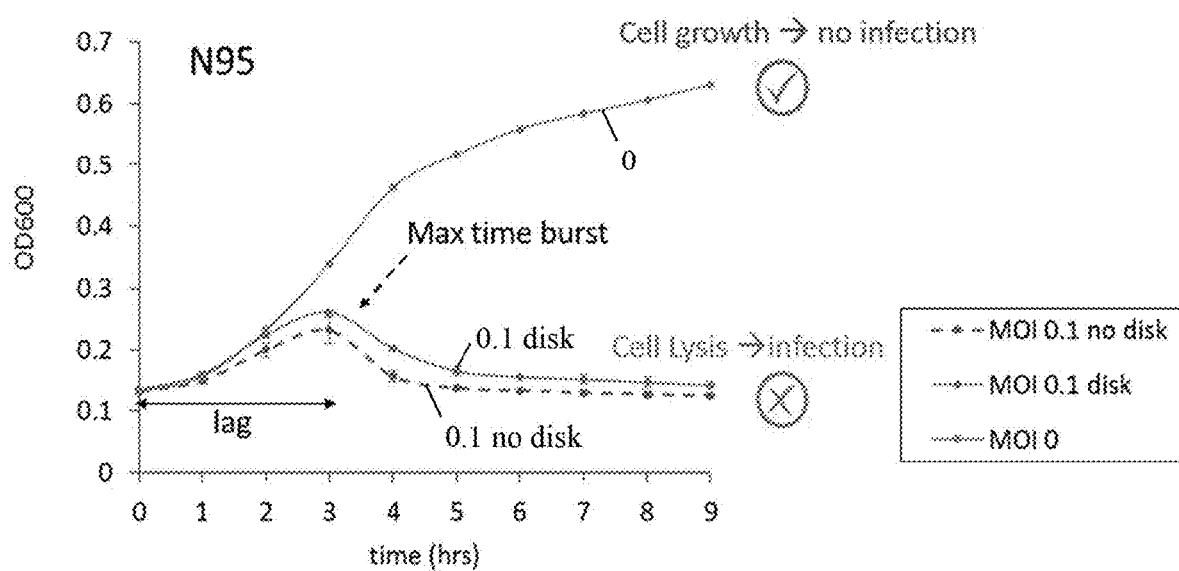
FIG. 9 shows a phage recovery assay for the N95 series showing the killing effect at various multiplicities of infection ("MOI"), defined by the ratio of virions to cells.

FIG. 9 shows a phage recovery assay for the N95 series showing the killing effect at various multiplicities of infection ("MOI"), defined by the ratio of virions to cells.

Figure 10:
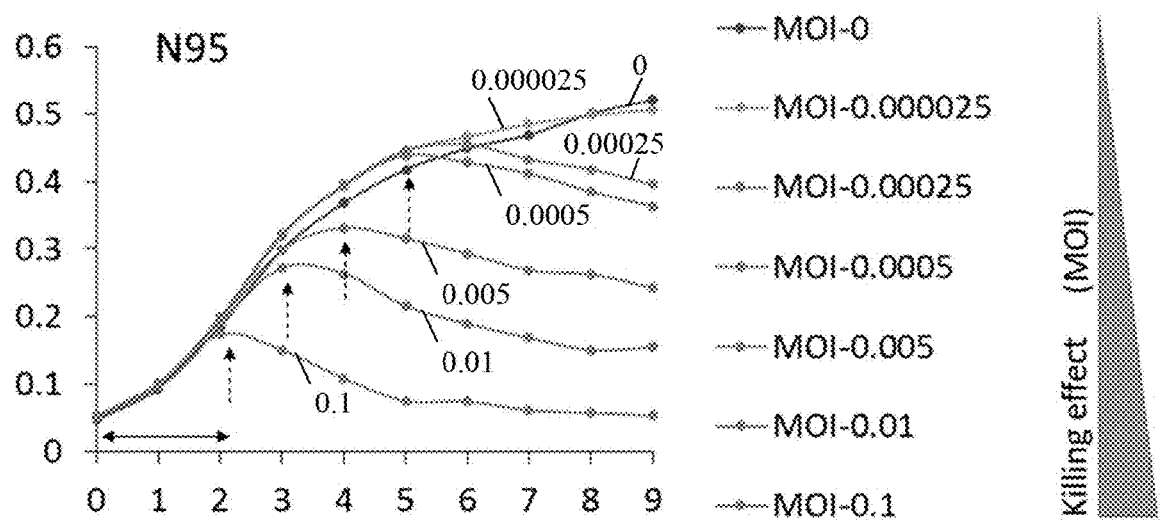
FIG. 10 shows a phage recovery assay for the N95 series showing the killing effect at various MOI.

FIG. 10 shows a phage recovery assay for the N95 series showing the killing effect at various MOI.

Figure 11A:
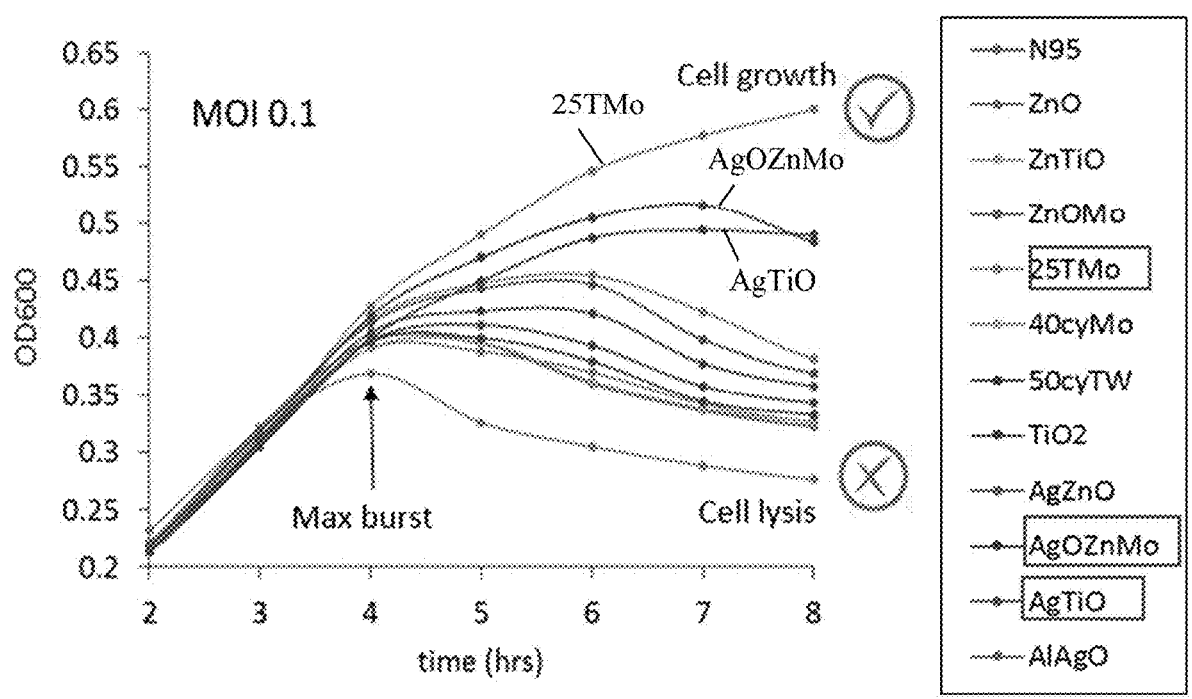
FIG. 11A shows a phage recovery assay for the N95 series for disks coated in the indicated materials and serial-diluted on disk. For a given MOI (here 0.1), bacterial growth is monitored over time after infection. After a lag time, (corresponding to few cycles of phage infection and release) all bacteria are infected (max burst) and start lysing, OD decrease will depend of phage infectivity of the culture.
Figure 11B:
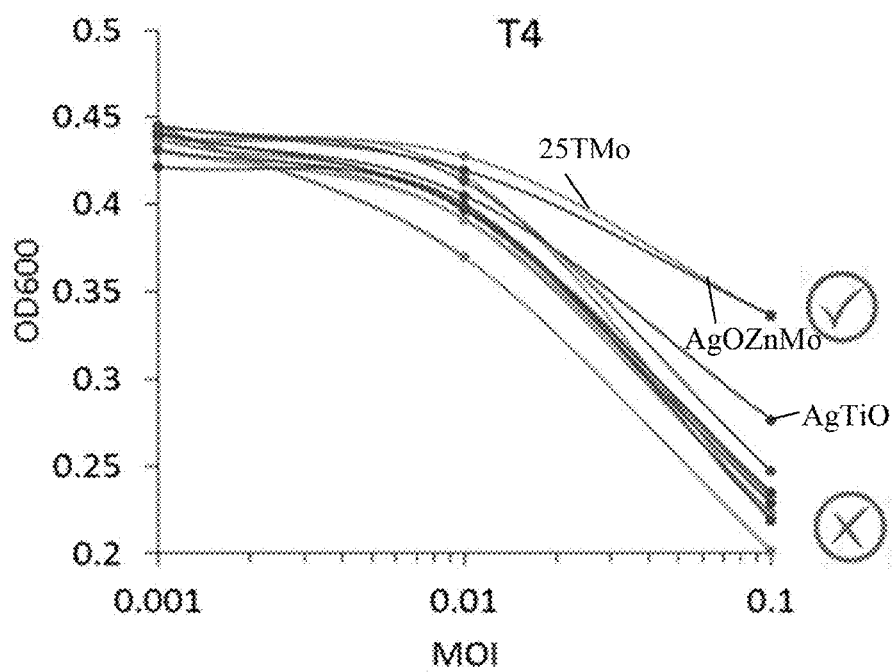
FIG. 11B shows a phage recovery assay for the N95 series for disks coated in the indicated materials and serial-diluted on disk. For a given time after infection (here 4 hours), OD is monitored as a function of MOI. Lysis starts showing after 4 hours of infection at a starting MOI>0.01. Those culture with a lower MOI (less phage recovery) will be delayed in lysis. Note: MOI here corresponds to the theoretical starting MOI at T0 (at the beginning of the culture).

FIG. 11A shows a phage recovery assay for the N95 series for disks coated in the indicated materials and serial-diluted on disk. For a given MOI (here 0.1), bacterial growth is monitored over time after infection. After a lag time, (corresponding to few cycles of phage infection and release) all bacteria are infected (max burst) and start lysing, OD decrease will depend of phage infectivity of the culture. FIG. 11B shows a phage recovery assay for the N95 series for disks coated in the indicated materials and serial-diluted on disk. For a given time after infection (here 4 hours), OD is monitored as a function of MOI. Lysis starts showing after 4 hours of infection at a starting MOI>0.01. Those culture with a lower MOI (less phage recovery) will be delayed in lysis. Note: MOI here corresponds to the theoretical starting MOI at T0 (at the beginning of the culture).

Figure 12A:
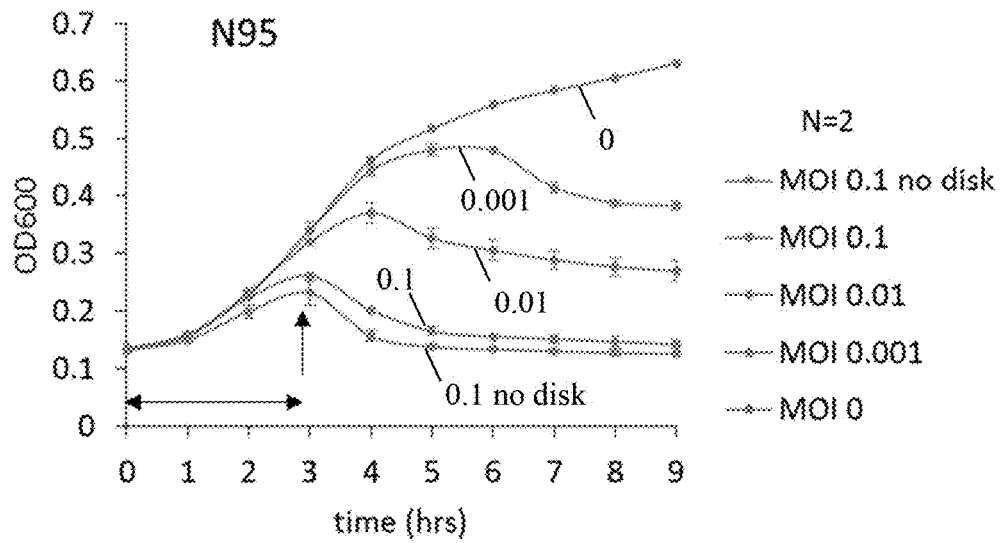
FIG. 12A shows a semi-quantitative assay for the N95 series at various MOI.
Figure 12B:
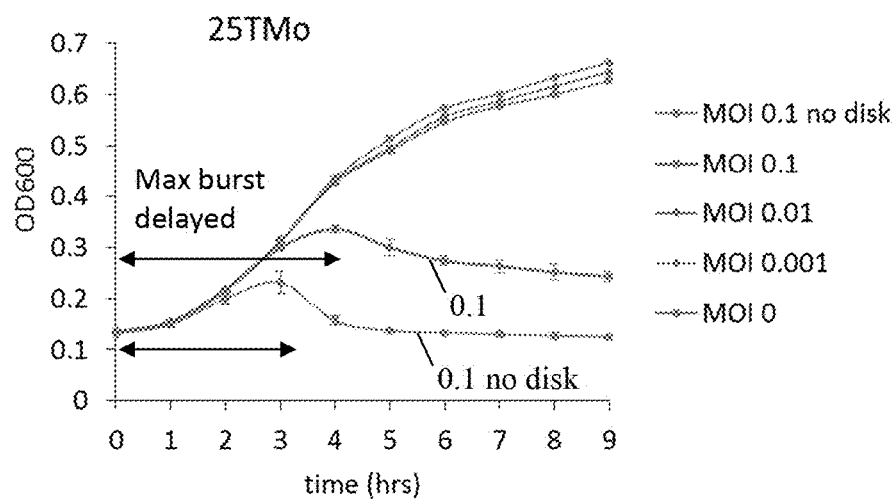
FIG. 12B shows a semi-quantitative assay for the 25TMo coating at various MOI.
Figure 12C:
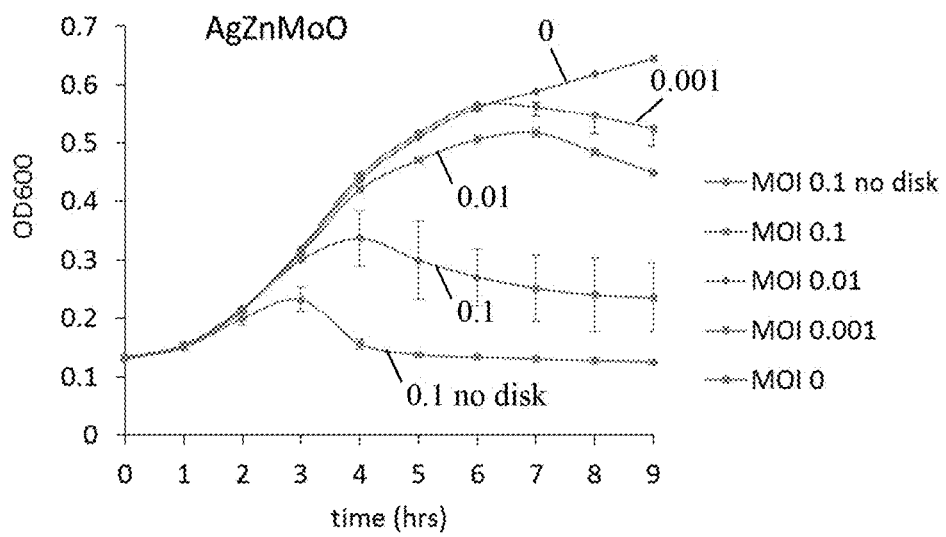
FIG. 12C shows a semi-quantitative assay for the AgZnMoO coating at various MOI.
Figure 12D:
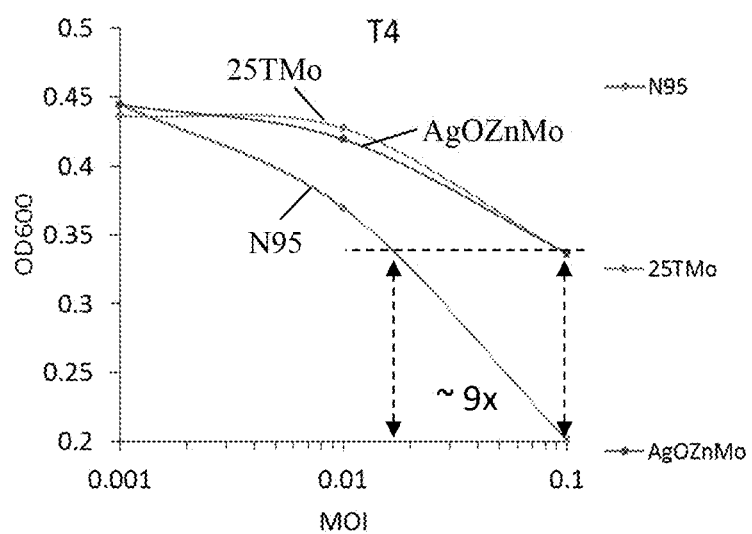
FIG. 12D compares the MOI for the N95 series, 25TMo coating, and AgZnMoO coating.

FIG. 12A shows a semi-quantitative assay for the N95 series at various MOI. FIG. 12B shows a semi-quantitative assay for the 25TMo coating at various MOI. FIG. 12C shows a semi-quantitative assay for the AgZnMoO coating at various MOI. FIG. 12D compares the MOI for the N95 series, 25TMo coating, and AgZnMoO coating.

Figure 13:
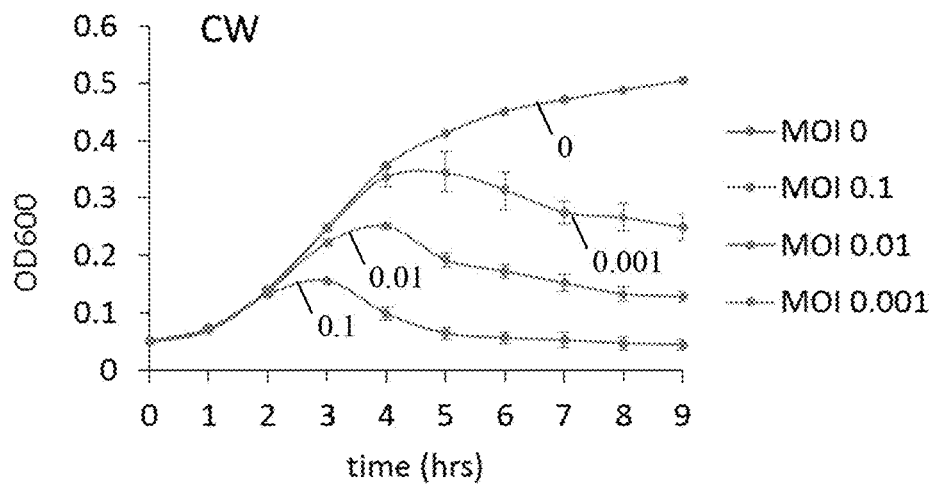
FIG. 13 shows a phage recovery assay for the CW series showing the killing effect at various MOI.

FIG. 13 shows a phage recovery assay for the CW series showing the killing effect at various MOI.

Figure 14A:
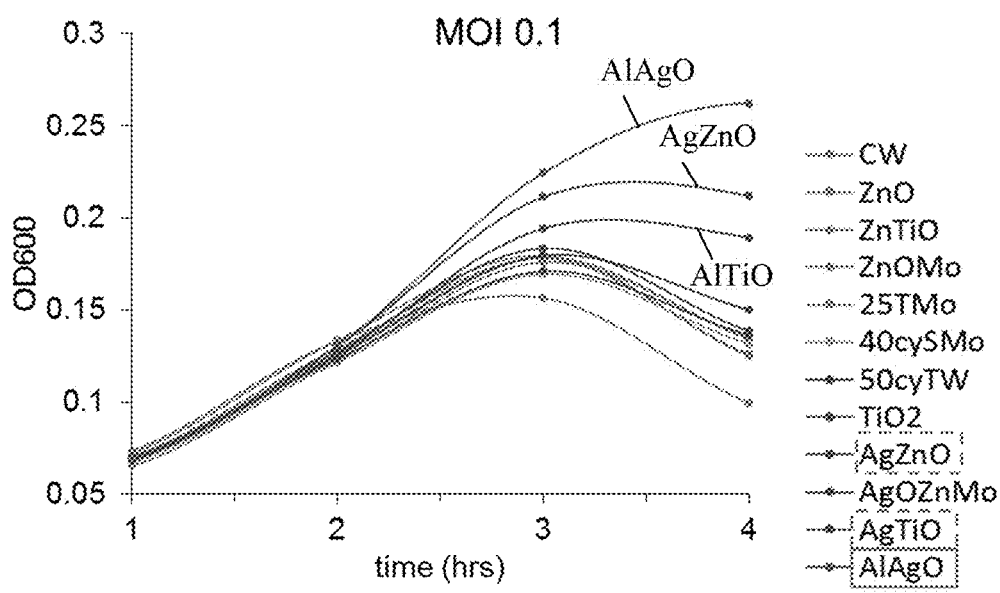
FIG. 14A shows a phage recovery assay for the CW series at MOI 0.1.
Figure 14B:
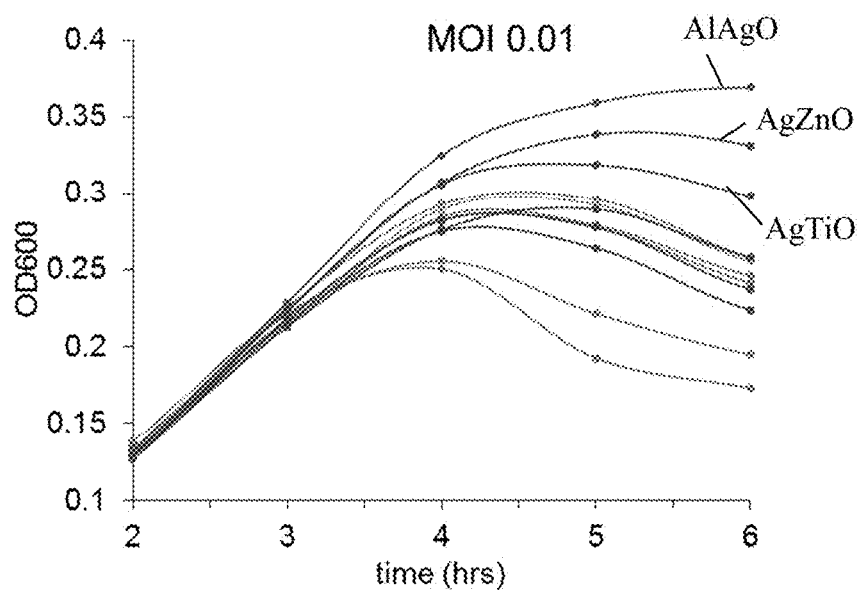
FIG. 14B shows a phage recovery assay for the CW series at MOI 0.01.
Figure 14C:
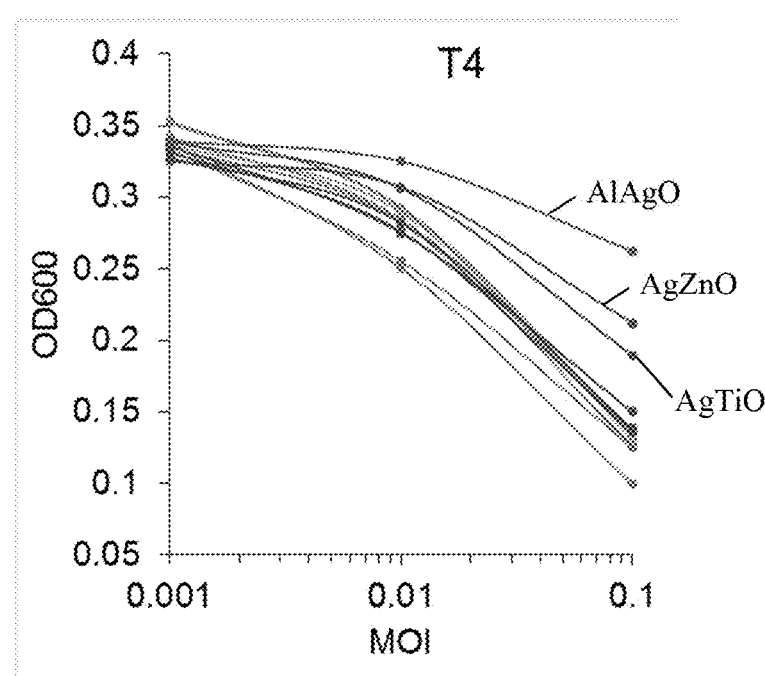
FIG. 14C compares the MOI for the CW series.

FIG. 14A shows a phage recovery assay for the CW series at MOI 0.1. FIG. 14B shows a phage recovery assay for the CW series at MOI 0.01. FIG. 14C compares the MOI for the CW series.

Figure 15A:
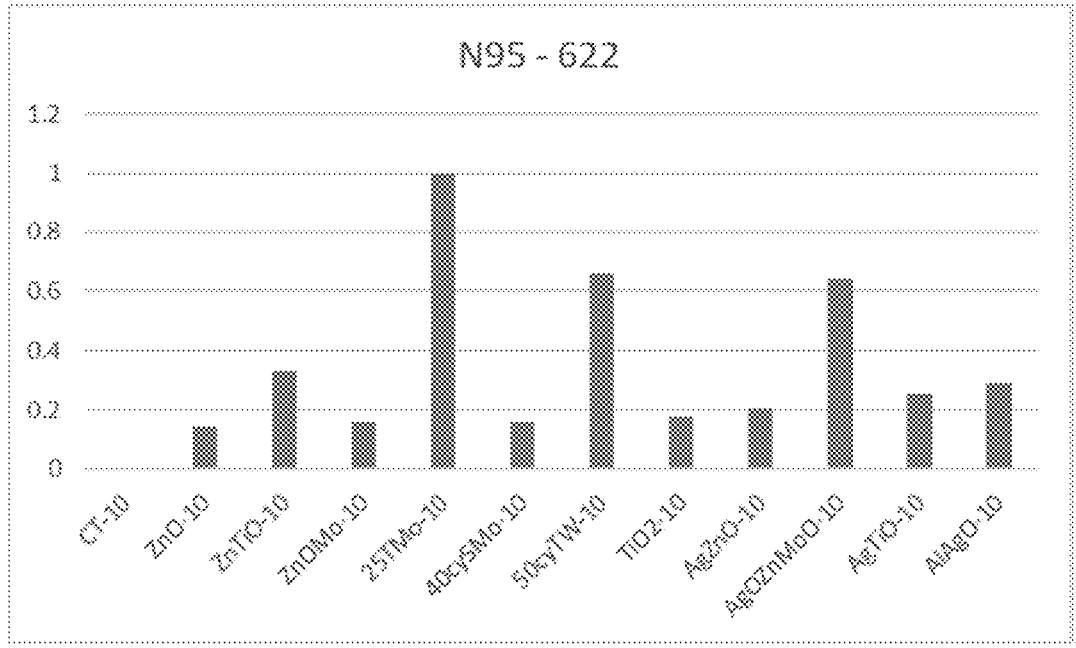
FIG. 15A shows an antiviral testing summary for the N95 series with the OD at MOI 0.1 for 8 hours.
Figure 15B:
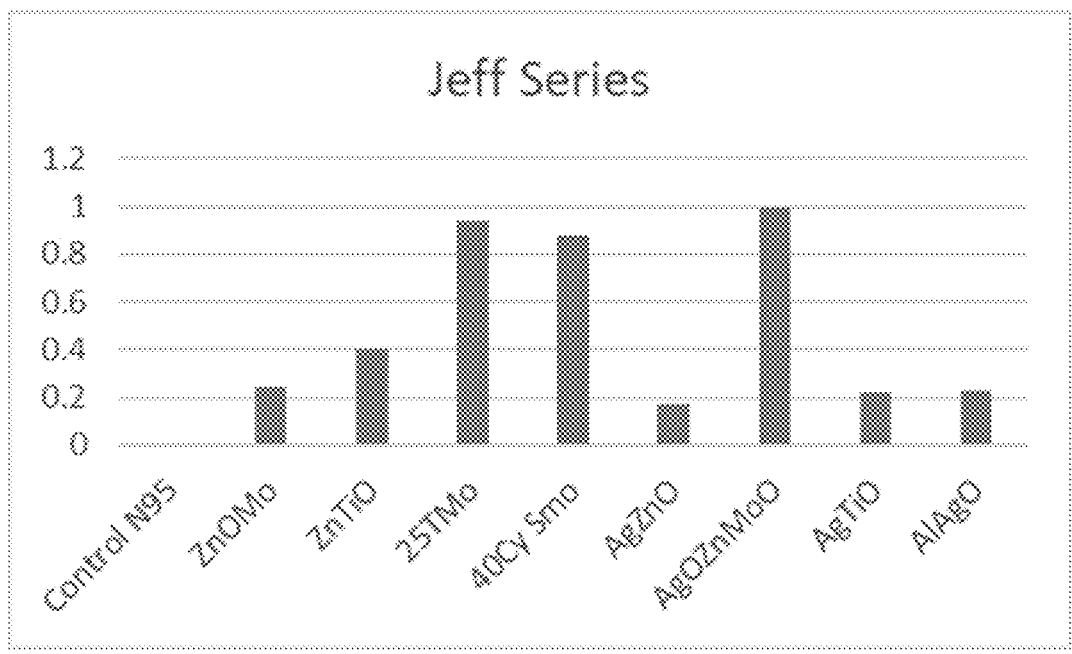
FIG. 15B shows an antiviral testing summary for the Jeff series with the OD at MOI 0.1 for 5 hours.
Figure 15C:
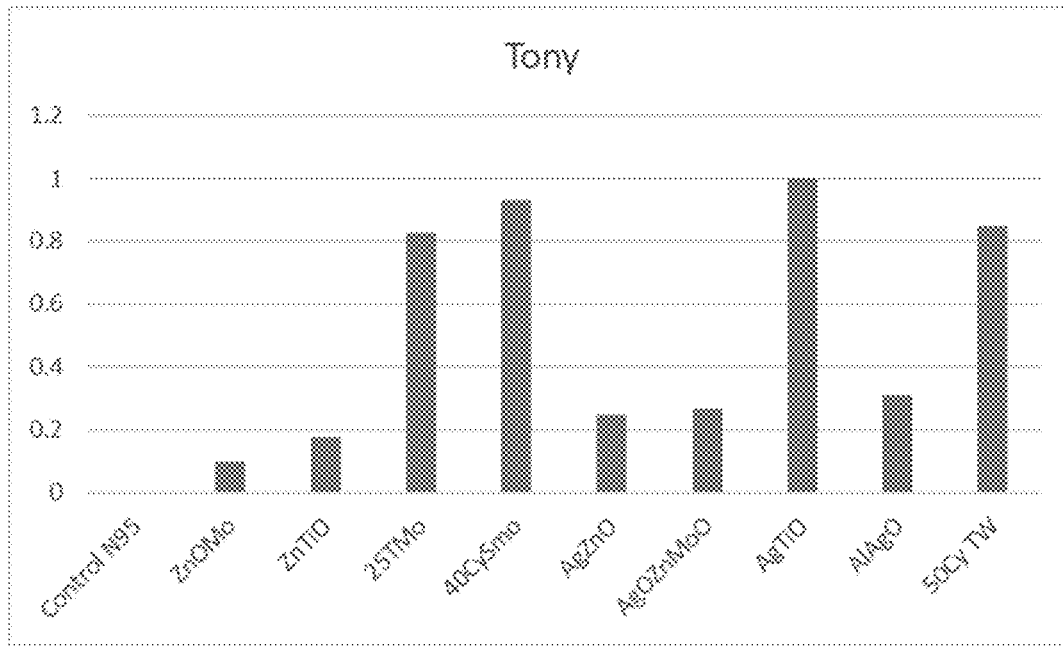
FIG. 15C shows an antiviral testing summary for the Tony series with the OD at MOI 0.1 for 5 hours.
Figure 15D:
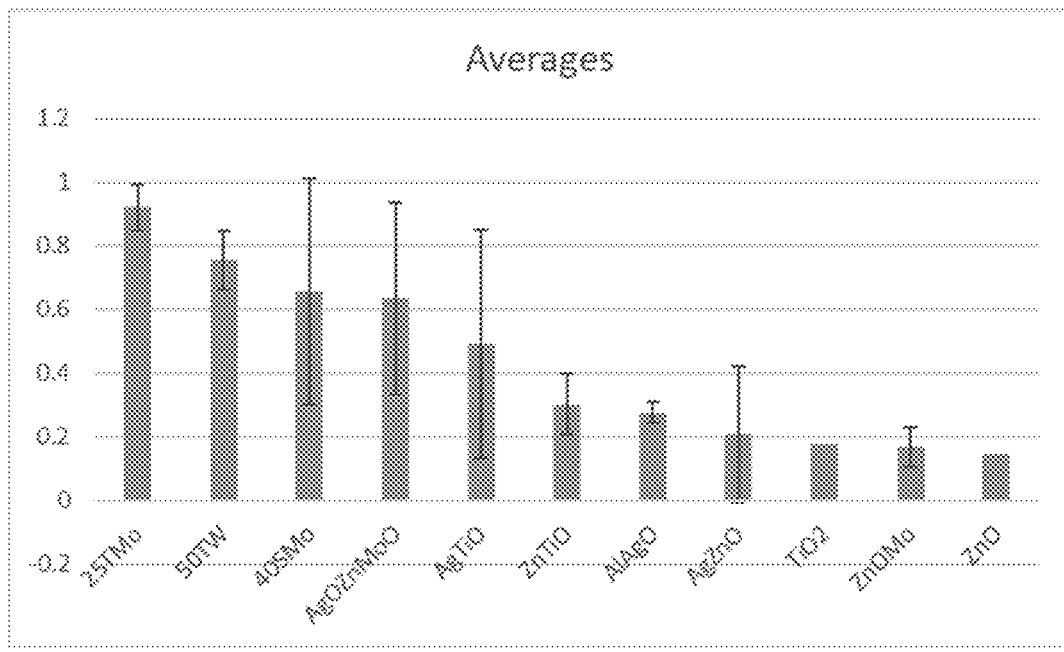
FIG. 15D shows the averages.

FIG. 15A shows an antiviral testing summary for the N95 series with the OD at MOI 0.1 for 8 hours. FIG. 15B shows an antiviral testing summary for the Jeff series with the OD at MOI 0.1 for 5 hours. FIG. 15C shows an antiviral testing summary for the Tony series with the OD at MOI 0.1 for 5 hours. FIG. 15D shows the averages.

Figure 16A:
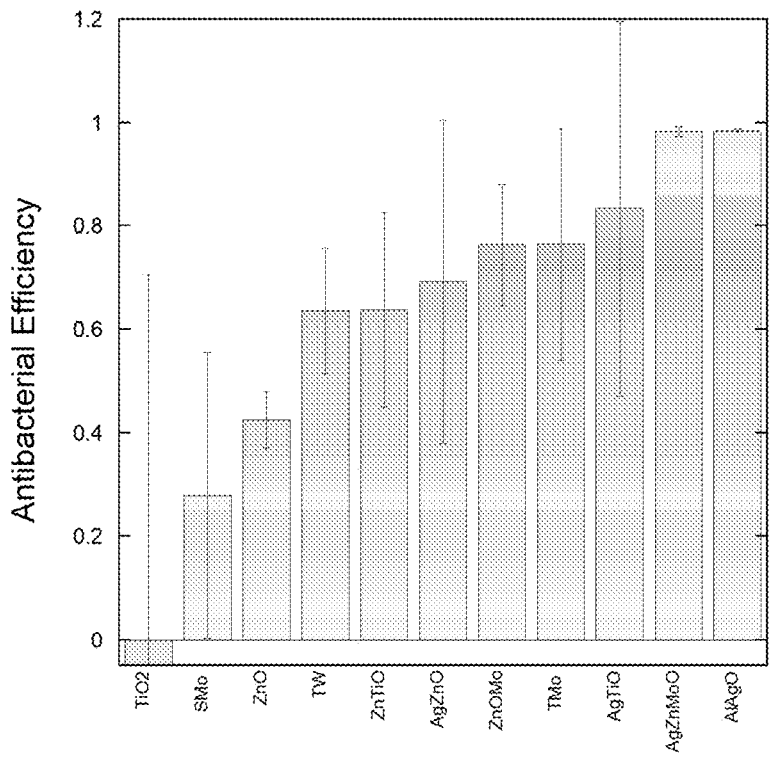
FIG. 16A shows the antibacterial efficiency for the indicated coatings.
Figure 16B:
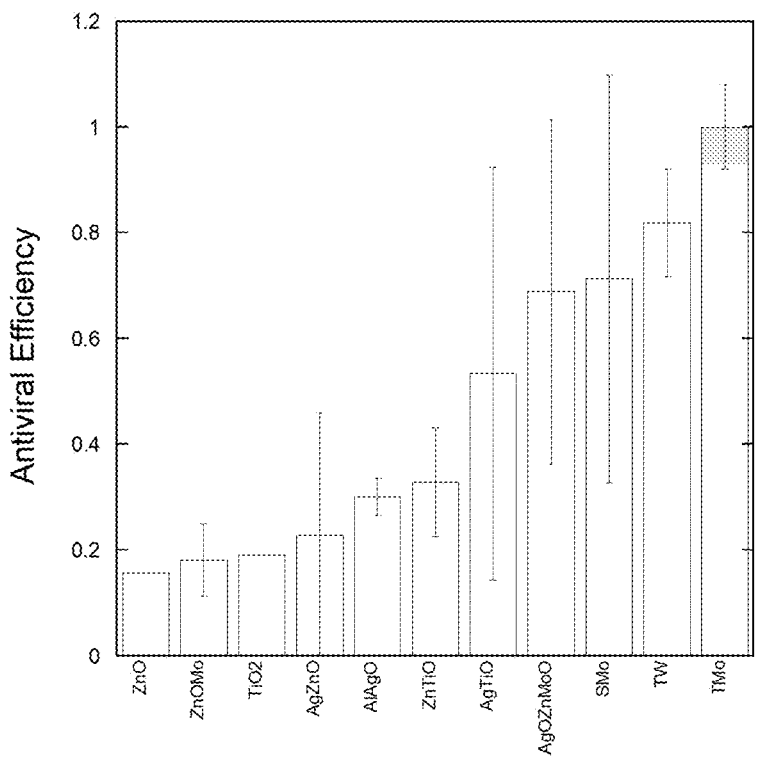
FIG. 16B shows the antiviral efficiency for the indicated coatings.
Figure 16C:
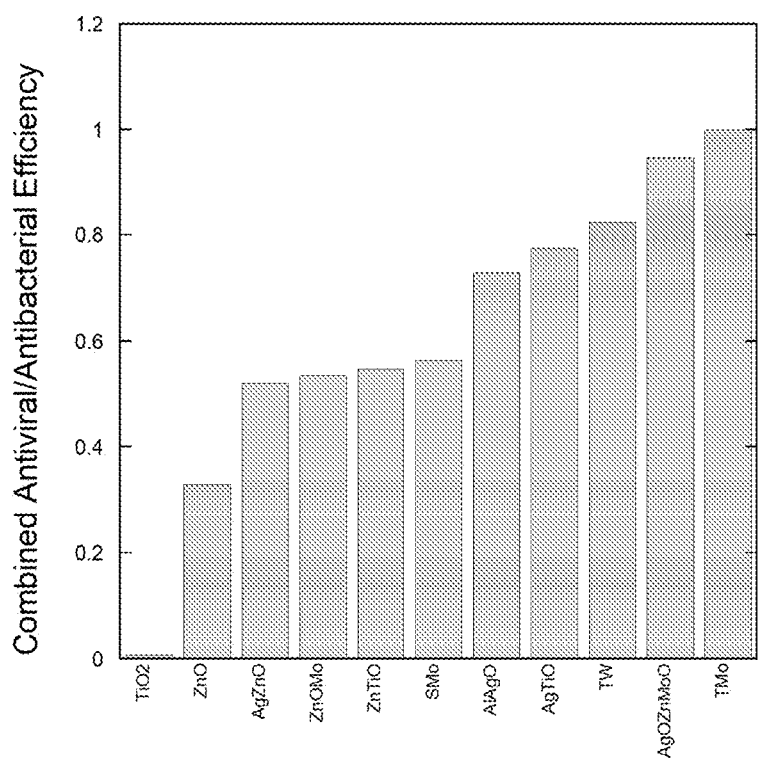
FIG. 16C shows the combined antibacterial/antibacterial efficiency for the indicated coatings.

FIG. 16A shows the antibacterial efficiency for the indicated coatings. FIG. 16B shows the antiviral efficiency for the indicated coatings. FIG. 16C shows the combined antibacterial/antibacterial efficiency for the indicated coatings.

Filtration Testing

Figure 17:
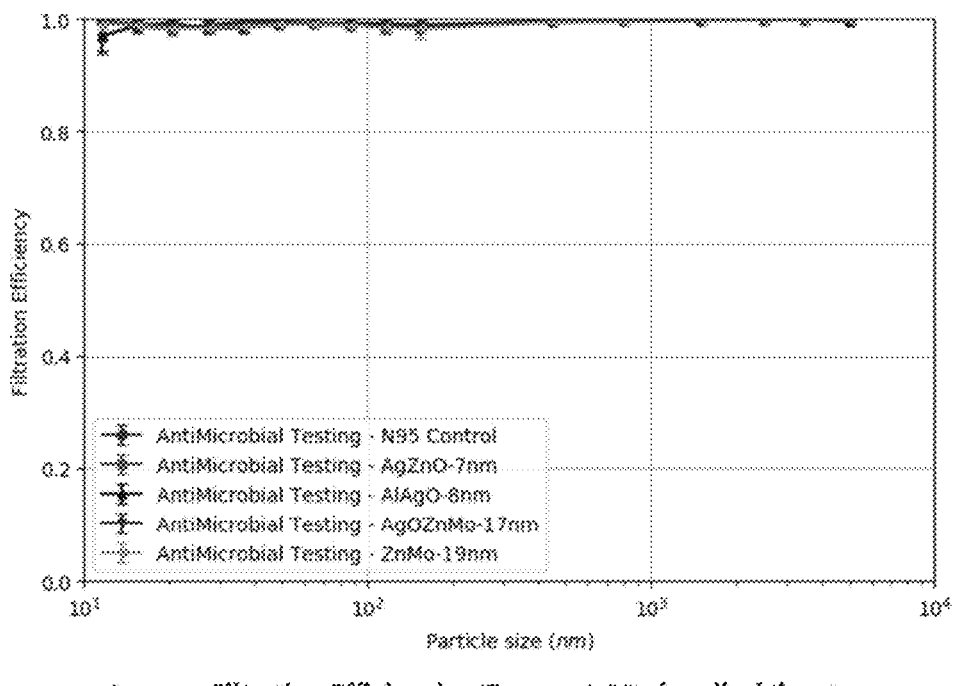
FIG. 17 shows the results of filtration testing of N95 materials for the indicated coatings.

FIG. 17 shows the results of filtration testing of N95 materials for the indicated coatings.

Definitions

No claim element herein is to be construed under the provisions of 35 U. S.C. § 112(f), unless the element is expressly recited using the phrase "means for."

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic. For example, circuit A communicably "coupled" to circuit B may signify that the circuit A communicates directly with circuit B (i.e., no intermediary) or communicates indirectly with circuit B (e.g., through one or more intermediaries).

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

What is claimed is:

1. A method depositing a metal or metal oxide comprising:
providing a base material in a reactor;
exposing, for 10-30 seconds, the base material to a pre-treatment metal precursor; and
after exposing the pre-treatment metal precursor, depositing a metal or metal oxide using sequential infiltration synthesis (SIS) process including at least one cycle of:
pulsing a first metal precursor, different from the pre-treatment metal precursor, into the reactor for a first metal precursor pulse time;
exposing the base material to the first metal precursor for a first metal precursor exposure time and at a first partial pressure, the first metal precursor infiltrating at least a portion of the base material and binding therein with the base material;
purging the reactor of the first metal precursor;
pulsing a co-reactant precursor into the reactor for a first co-reactant pulse time;
exposing the base material to the co-reactant precursor for a co-reactant precursor exposure time and at a second partial pressure, the co-reactant precursor infiltrating at least a portion of the base material and binding therein to form the metal or metal oxide; and purging the reactor of the co-reactant precursor.

2. The method of claim 1, wherein the first metal precursor pulse time is 2-4 seconds.

3. The method of claim 1, wherein the pre-treatment metal precursor is exposed for 12-16 seconds.

4. The method of claim 1, wherein the co-reactant precursor pulse time is greater than 2 seconds to 4 seconds.

5. The method of claim 1, wherein purging the reactor of the co-reactant precursor proceeds for greater than 0 seconds to 500 seconds and comprises reducing the pressure within the reactor to substantially a vacuum.

6. The method of claim 1, wherein the base material comprises polypropylene, polyethylene, polyester, polysulfone, polyethersulfone, polyurethane, polyvinylidene fluoride, or polytetrafluoroethylene.

7. The method of claim 1, wherein the metal or metal oxide comprises a material selected from the group consisting of: zinc titanium oxide (ZnTiO), molybdenum (Mo), tungsten (W), sliver (Ag), silver oxide (AgO), silver aluminum oxide (AgAlO), silver zinc oxide (AgZnO), molybdenum zinc oxide (MoZnO), and aluminum molybdenum oxyfluoride (AlMoOF).

8. The method of claim 1, wherein the pre-treatment metal precursor is exposed for 10-30 seconds and the first metal precursor pulse time is 2-4 seconds.

9. A method depositing a metal or metal oxide comprising:

providing a base material in a reactor;

exposing the base material to a pre-treatment metal precursor and after exposing the pre-treatment metal precursor, depositing a metal or metal oxide using atomic layer deposition process including at least one cycle of:

pulsing a first metal precursor, different from the pre-treatment metal precursor, into the reactor for a first metal precursor pulse time;

exposing the base material to the first metal precursor for a first metal precursor exposure time and at a first partial pressure, the first metal precursor binding on the base material;

purging the reactor of the first metal precursor;

pulsing a co-reactant precursor into the reactor for a first co-reactant pulse time;

exposing the base material to the co-reactant precursor for a co-reactant precursor exposure time and at a second partial pressure, the co-reactant precursor reacting with the bound first metal precursor to form the metal or metal oxide; and purging the reactor of the co-reactant precursor.

10. The method of claim 9, wherein the first metal precursor pulse time 2-4 seconds.

11. The method of claim 9, wherein the pre-treatment metal precursor is exposed for 10-30 seconds.

12. The method of claim 11, wherein the pre-treatment metal precursor is exposed for 12-16 seconds.

13. The method of claim 9, wherein the co-reactant precursor pulse time is greater than 2 seconds to 4 seconds.

14. The method of claim 9, wherein purging the reactor of the co-reactant precursor proceeds for greater than 0 seconds to 500 seconds and comprises reducing the pressure within the reactor to substantially a vacuum.

15. The method of claim 9, wherein the base material comprises polypropylene, polyethylene, polyester, polysulfone, polyethersulfone, polyurethane, polyvinylidene fluoride, or polytetrafluoroethylene.

16. The method of claim 9, wherein the metal or metal oxide comprises a material selected from the group consisting of: zinc titanium oxide (ZnTiO), molybdenum (Mo), tungsten (W), sliver (Ag), silver oxide (AgO), silver aluminum oxide (AgAlO), silver zinc oxide (AgZnO), molybdenum zinc oxide (MoZnO), and aluminum molybdenum oxyfluoride (AlMoOF).

* * * * *